US012779187B2

(12) United States Patent
Nguyen et al.

(10) Patent No.: US 12,779,187 B2
(45) Date of Patent: Nov. 3, 2026

(54) DILATOR WITH ENCAPSULATION FEATURE FOR SHEATH TIPS

(71) Applicant: EDWARDS LIFESCIENCES CORPORATION, Irvine, CA (US)

(72) Inventors: Hien T. Nguyen, Aliso Viejo, CA (US); Anne Bernadette Aragon Alcasid, Costa Mesa, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 74 days.

(21) Appl. No.: 18/802,091

(22) Filed: Aug. 13, 2024

(65) Prior Publication Data

US 2025/0001146 A1 Jan. 2, 2025

Related U.S. Application Data

(63) Continuation of application No. PCT/US2023/013672, filed on Feb. 23, 2023.

(60) Provisional application No. 63/314,961, filed on Feb. 28, 2022.

(51) Int. Cl.
*A61M 29/00* (2006.01)

(52) U.S. Cl.
CPC ..... *A61M 29/00* (2013.01); *A61M 2205/0266* (2013.01)

(58) Field of Classification Search
CPC .............. A61M 29/00; A61M 25/0662; A61M 2205/0266; A61F 2/95; A61B 17/3415; A61B 17/3431; A61B 2017/00778; A61B 2017/00867
See application file for complete search history.

(56) References Cited

U.S. PATENT DOCUMENTS

| | | | |
|---|---|---|---|
| 519,297 | A | 5/1894 | Wanek et al. |
| 4,035,849 | A | 7/1977 | Angell et al. |
| 4,592,340 | A | 6/1986 | Boyles |
| 4,601,713 | A | 7/1986 | Fuqua |

(Continued)

FOREIGN PATENT DOCUMENTS

| | | | |
|---|---|---|---|
| CN | 107280718 | A | 10/2017 |
| DE | 19532846 | A1 | 3/1997 |

(Continued)

OTHER PUBLICATIONS

Tamburino, C. et al., Percutaneous Treatment of Left Side Cardiac Valves: A Practical Guide for the Interventional Cardiologist—Third Edition, Germany, Springer International Publishing, 2018, pp. 1-534.

*Primary Examiner* — Kathleen S Holwerda
*Assistant Examiner* — Cherie M Poland
(74) *Attorney, Agent, or Firm* — Chang & Hale LLP

(57) ABSTRACT

Dilators and introducers that include encapsulation features configured to couple to an access sheath are described herein. For example, a dilator can include an elongate shaft configured to be received within an access sheath. The elongate shaft can be tapered towards a distal end of the elongate shaft. The dilator can also include an encapsulation feature disposed on a distal portion of the elongate shaft. The encapsulation feature can include a plurality of tabs that extend longitudinally. The plurality of tabs can be configured to cover a distal end of the access sheath when the elongate shaft is disposed within the access sheath.

20 Claims, 10 Drawing Sheets

(56) References Cited

U.S. PATENT DOCUMENTS 4,710,181 A 12/1987 Fuqua
4,738,666 A 4/1988 Fuqua
4,921,479 A 5/1990 Grayzel
4,955,895 A 9/1990 Sugiyama et al.
4,994,077 A 2/1991 Dobben
5,059,177 A 10/1991 Towne et al.
5,104,388 A 4/1992 Quackenbush
5,176,698 A 1/1993 Burns et al.
5,192,297 A 3/1993 Hull
5,266,073 A 11/1993 Wall
5,318,588 A 6/1994 Horzewski et al.
5,320,611 A 6/1994 Bonutti et al.
5,325,845 A 7/1994 Adair
5,358,496 A 10/1994 Ortiz et al.
5,411,552 A 5/1995 Andersen et al.
5,501,667 A 3/1996 Verduin, Jr.
5,554,185 A 9/1996 Block et al.
5,591,195 A 1/1997 Taheri et al.
5,599,305 A 2/1997 Hermann et al.
5,632,760 A 5/1997 Sheiban et al.
5,639,274 A 6/1997 Fischell et al.
5,674,240 A 10/1997 Bonutti et al.
5,728,068 A 3/1998 Leone et al.
5,749,890 A 5/1998 Shaknovich
5,782,809 A 7/1998 Umeno et al.
5,810,776 A 9/1998 Bacich et al.
5,817,100 A 10/1998 Igaki
5,824,044 A 10/1998 Quiachon et al.
5,840,081 A 11/1998 Andersen et al.
5,882,345 A 3/1999 Yoon
5,908,405 A 6/1999 Imran et al.
5,916,147 A 6/1999 Boury
5,944,690 A 8/1999 Falwell et al.
5,961,536 A 10/1999 Mickley et al.
5,968,068 A 10/1999 Dehdashtian et al.
5,997,508 A 12/1999 Lunn et al.
6,019,777 A 2/2000 Mackenzie
6,027,510 A 2/2000 Alt
6,033,381 A 3/2000 Kontos
6,080,141 A 6/2000 Castro et al.
6,090,072 A 7/2000 Kratoska et al.
6,090,136 A 7/2000 McDonald et al.
6,143,016 A 11/2000 Bleam et al.
6,162,208 A 12/2000 Hipps
6,168,614 B1 1/2001 Andersen et al.
6,174,327 B1 1/2001 Mertens et al.
6,190,357 B1 2/2001 Ferrari et al.
6,217,585 B1 4/2001 Houser et al.
6,235,050 B1 5/2001 Quiachon et al.
6,251,092 B1 6/2001 Qin et al.
6,312,443 B1 11/2001 Stone
6,346,092 B1 2/2002 Leschinsky
6,358,238 B1 3/2002 Sherry
6,379,372 B1 4/2002 Dehdashtian et al.
6,383,171 B1 5/2002 Gifford et al.
6,443,979 B1 9/2002 Stalker et al.
6,454,799 B1 9/2002 Schreck
6,458,153 B1 10/2002 Bailey et al.
6,461,382 B1 10/2002 Cao
6,471,672 B1 10/2002 Brown et al.
6,494,860 B2 12/2002 Rocamora et al.
6,500,147 B2 12/2002 Omaleki et al.
6,514,228 B1 2/2003 Hamilton et al.
6,527,979 B2 3/2003 Constantz et al.
6,579,305 B1 6/2003 Lashinski
6,582,462 B1 6/2003 Andersen et al.
6,632,236 B2 10/2003 Hogendijk
6,652,492 B1 11/2003 Bell et al.
6,652,578 B2 11/2003 Bailey et al.
6,730,118 B2 5/2004 Spenser et al.
6,733,525 B2 5/2004 Yang et al.
6,764,504 B2 7/2004 Wang et al.
6,767,362 B2 7/2004 Schreck
6,814,715 B2 11/2004 Bonutti et al.
6,830,584 B1 12/2004 Seguin
6,893,460 B2 5/2005 Spenser et al.
6,899,727 B2 5/2005 Armstrong et al.
6,908,481 B2 6/2005 Cribier
7,011,094 B2 3/2006 Rapacki et al.
7,018,406 B2 3/2006 Seguin et al.
7,018,408 B2 3/2006 Bailey et al.
7,137,993 B2 11/2006 Acosta et al.
7,276,084 B2 10/2007 Yang et al.
7,318,278 B2 1/2008 Zhang et al.
7,320,702 B2 1/2008 Hammersmark et al.
7,320,704 B2 1/2008 Lashinski et al.
7,374,571 B2 5/2008 Pease et al.
7,393,360 B2 7/2008 Spenser et al.
7,435,257 B2 10/2008 Lashinski et al.
7,438,712 B2 10/2008 Chouinard
7,510,575 B2 3/2009 Spenser et al.
7,585,321 B2 9/2009 Cribier
7,591,832 B2 9/2009 Eversull et al.
7,594,926 B2 9/2009 Linder et al.
7,597,709 B2 10/2009 Goodin
7,618,446 B2 11/2009 Andersen et al.
7,655,016 B2 2/2010 Demarais et al.
7,678,128 B2 3/2010 Boyle et al.
7,713,193 B2 5/2010 Nance et al.
7,762,995 B2 7/2010 Eversull et al.
7,766,820 B2 8/2010 Core
7,780,692 B2 8/2010 Nance et al.
7,780,723 B2 8/2010 Taylor
7,785,360 B2 8/2010 Freitag
7,785,366 B2 8/2010 Maurer et al.
7,837,692 B2 11/2010 Mulholland et al.
7,892,203 B2 2/2011 Lenker et al.
7,927,309 B2 4/2011 Palm
7,959,661 B2 6/2011 Hijlkema et al.
7,963,952 B2 6/2011 Wright, Jr. et al.
8,029,556 B2 10/2011 Rowe
8,034,072 B2 10/2011 Nguyen et al.
8,048,034 B2 11/2011 Eversull et al.
8,090,936 B2 1/2012 Fallon et al.
8,092,481 B2 1/2012 Nance et al.
8,167,932 B2 5/2012 Bourang et al.
8,252,015 B2 8/2012 Leeflang et al.
8,282,664 B2 10/2012 Nance et al.
RE43,882 E 12/2012 Hopkins et al.
8,414,645 B2 4/2013 Dwork et al.
8,449,606 B2 5/2013 Eliasen et al.
8,475,523 B2 7/2013 Duffy
8,562,559 B2 10/2013 Bishop et al.
8,562,673 B2 10/2013 Yeung et al.
8,568,472 B2 10/2013 Marchand et al.
8,652,203 B2 2/2014 Quadri et al.
8,668,668 B2 3/2014 Bishop et al.
8,690,936 B2 4/2014 Nguyen et al.
8,790,387 B2 7/2014 Nguyen et al.
9,044,577 B2 6/2015 Bishop et al.
9,061,119 B2 6/2015 Le et al.
9,119,716 B2 9/2015 Lee et al.
9,192,751 B2 11/2015 Macaulay et al.
9,192,752 B2 11/2015 Leeflang et al.
9,254,374 B2 2/2016 Thorstenson et al.
9,259,813 B2 2/2016 Heideman et al.
9,301,840 B2 4/2016 Nguyen et al.
9,301,841 B2 4/2016 Nguyen et al.
9,320,508 B2 4/2016 Carroux
9,393,041 B2 7/2016 Barker et al.
9,642,704 B2 5/2017 Tuval et al.
9,788,944 B2 10/2017 Daly et al.
9,795,477 B2 10/2017 Tran et al.
9,907,931 B2 3/2018 Birmingham et al.
10,327,896 B2 6/2019 Zhou et al.
10,639,152 B2 5/2020 Le et al.
10,792,471 B2 10/2020 Zhou et al.
10,912,919 B2 2/2021 Bulman et al.
11,273,038 B2 3/2022 Tang et al.
11,344,698 B2 5/2022 Worthley et al.
2001/0002445 A1 5/2001 Vesely
2001/0007082 A1 7/2001 Dusbabek et al.
2001/0012950 A1 8/2001 Nishtala et al.
2002/0032459 A1 3/2002 Horzewski et al.

(56) References Cited

U.S. PATENT DOCUMENTS

2002/0032481 A1 3/2002 Gabbay
2002/0058995 A1 5/2002 Stevens
2002/0099431 A1 7/2002 Armstrong et al.
2002/0123793 A1 9/2002 Schaldach et al.
2002/0128702 A1 9/2002 Menz et al.
2002/0165461 A1 11/2002 Hayzelden et al.
2003/0004537 A1 1/2003 Boyle et al.
2003/0014068 A1 1/2003 Bonutti et al.
2003/0040792 A1 2/2003 Gabbay
2003/0050694 A1 3/2003 Yang et al.
2003/0120341 A1 6/2003 Shennib et al.
2004/0087968 A1 5/2004 Core
2004/0093061 A1 5/2004 Acosta et al.
2004/0122415 A1 6/2004 Johnson
2004/0133263 A1 7/2004 Dusbabek et al.
2004/0143197 A1 7/2004 Soukup et al.
2004/0186563 A1 9/2004 Lobbi
2004/0186565 A1 9/2004 Schreck
2004/0260389 A1 12/2004 Case et al.
2005/0080430 A1 4/2005 Wright et al.
2005/0080474 A1 4/2005 Andreas et al.
2005/0085842 A1 4/2005 Eversull et al.
2005/0096736 A1 5/2005 Osse et al.
2005/0125021 A1 6/2005 Nance et al.
2005/0137689 A1 6/2005 Salahieh et al.
2005/0149160 A1 7/2005 McFerran
2005/0203614 A1 9/2005 Forster et al.
2005/0203617 A1 9/2005 Forster et al.
2005/0245894 A1 11/2005 Azizi
2006/0020321 A1 1/2006 Parker
2006/0025857 A1 2/2006 Bergheim et al.
2006/0135962 A1 6/2006 Kick et al.
2006/0135981 A1 6/2006 Lenker et al.
2006/0217755 A1 9/2006 Eversull et al.
2006/0282150 A1 12/2006 Olson et al.
2007/0005131 A1 1/2007 Taylor
2007/0021768 A1 1/2007 Nance et al.
2007/0073389 A1 3/2007 Bolduc et al.
2007/0074805 A1 4/2007 Leeflang et al.
2007/0087148 A1 4/2007 Okushi et al.
2007/0088431 A1 4/2007 Bourang et al.
2007/0100356 A1 5/2007 Lucatero et al.
2007/0112422 A1 5/2007 Dehdashtian
2007/0203575 A1 8/2007 Forster et al.
2007/0219612 A1 9/2007 Andreas et al.
2007/0239254 A1 10/2007 Chia et al.
2007/0244546 A1 10/2007 Francis
2007/0265700 A1 11/2007 Eliasen et al.
2008/0004521 A1 1/2008 Hundley et al.
2008/0004571 A1 1/2008 Voss
2008/0065011 A1 3/2008 Marchand et al.
2008/0103520 A1 5/2008 Selkee
2008/0114331 A1 5/2008 Holman et al.
2008/0125853 A1 5/2008 Bailey et al.
2008/0200943 A1* 8/2008 Barker ............... A61B 17/3431 606/191
2008/0243081 A1 10/2008 Nance et al.
2008/0294230 A1 11/2008 Parker
2009/0024428 A1 1/2009 Hudock
2009/0069889 A1 3/2009 Suri et al.
2009/0138079 A1 5/2009 Tuval et al.
2009/0157175 A1 6/2009 Benichou
2009/0182411 A1 7/2009 Irwin et al.
2009/0192585 A1 7/2009 Bloom et al.
2009/0228093 A1 9/2009 Taylor et al.
2009/0240202 A1 9/2009 Drasler et al.
2009/0276040 A1 11/2009 Rowe et al.
2009/0281619 A1 11/2009 Le et al.
2009/0287182 A1 11/2009 Bishop et al.
2009/0299456 A1 12/2009 Melsheimer
2009/0319037 A1 12/2009 Rowe et al.
2010/0030318 A1 2/2010 Berra
2010/0036472 A1 2/2010 Papp
2010/0036473 A1 2/2010 Roth
2010/0049313 A1 2/2010 Alon et al.
2010/0076402 A1 3/2010 Mazzone et al.
2010/0076541 A1 3/2010 Kumoyama
2010/0082089 A1 4/2010 Quadri et al.
2010/0094209 A1 4/2010 Drasler et al.
2010/0094392 A1 4/2010 Nguyen et al.
2010/0094394 A1 4/2010 Beach et al.
2010/0121425 A1 5/2010 Shimada
2010/0145429 A1 6/2010 Dhoke et al.
2010/0145431 A1 6/2010 Wu et al.
2010/0161036 A1 6/2010 Pintor et al.
2010/0174363 A1 7/2010 Castro
2010/0198160 A1 8/2010 Voss
2010/0198347 A1 8/2010 Zakay et al.
2010/0274344 A1 10/2010 Dusbabek et al.
2010/0324490 A1 12/2010 Pini et al.
2011/0015729 A1 1/2011 Jimenez et al.
2011/0054596 A1 3/2011 Taylor
2011/0112567 A1 5/2011 Lenker et al.
2011/0137331 A1 6/2011 Walsh et al.
2011/0160846 A1 6/2011 Bishop et al.
2011/0190697 A1 8/2011 Farnan
2011/0251681 A1 10/2011 Shipley et al.
2012/0083877 A1 4/2012 Nguyen et al.
2012/0116439 A1 5/2012 Ho
2012/0123529 A1 5/2012 Levi et al.
2012/0158033 A1 6/2012 Deal et al.
2012/0239142 A1 9/2012 Liu et al.
2012/0323180 A1 12/2012 Chebator et al.
2013/0030519 A1 1/2013 Tran et al.
2013/0090624 A1 4/2013 Munsinger
2013/0131718 A1 5/2013 Jenson et al.
2013/0178711 A1 7/2013 Avneri et al.
2013/0211324 A1 8/2013 Voss et al.
2013/0231735 A1 9/2013 Deem et al.
2013/0268064 A1 10/2013 Duffy
2013/0281787 A1 10/2013 Avneri et al.
2013/0317598 A1 11/2013 Rowe et al.
2014/0012281 A1 1/2014 Wang et al.
2014/0121629 A1 5/2014 Macaulay et al.
2014/0142509 A1 5/2014 Bonutti et al.
2014/0142688 A1* 5/2014 Duffy .................... A61F 2/2436 623/2.11
2014/0236122 A1 8/2014 Anderson et al.
2014/0236123 A1 8/2014 Birmingham et al.
2014/0257455 A1 9/2014 Puckett et al.
2014/0296962 A1 10/2014 Cartledge et al.
2014/0379067 A1 12/2014 Nguyen et al.
2015/0112428 A1 4/2015 Daly et al.
2015/0165158 A1 6/2015 Ren et al.
2015/0182723 A1 7/2015 Leeflang et al.
2015/0238178 A1 8/2015 Carroux
2015/0265798 A1 9/2015 Nihonmatsu et al.
2015/0320971 A1 11/2015 Leeflang et al.
2016/0074067 A1 3/2016 Furnish et al.
2016/0128723 A1 5/2016 Ginn et al.
2016/0135840 A1 5/2016 Kick et al.
2016/0213882 A1 7/2016 Fitterer et al.
2016/0296332 A1 10/2016 Zhou et al.
2016/0296730 A1 10/2016 Zhou et al.
2017/0014157 A1 1/2017 Coyle et al.
2017/0065415 A1 3/2017 Rupp et al.
2017/0072163 A1 3/2017 Lim et al.
2017/0196690 A1 7/2017 Racchini et al.
2017/0209133 A1 7/2017 Ciulla et al.
2017/0245864 A1 8/2017 Franano et al.
2017/0252062 A1 9/2017 Fitterer et al.
2018/0043133 A1 2/2018 Wong
2018/0153689 A1 6/2018 Maimon et al.
2018/0161064 A1 6/2018 Fitterer et al.
2018/0199960 A1 7/2018 Anderson et al.
2018/0200490 A1* 7/2018 Gianotti ................ A61M 29/00
2018/0207395 A1 7/2018 Bulman et al.
2018/0229000 A1 8/2018 Anderson et al.
2018/0325549 A1 11/2018 Thoreson et al.
2018/0344456 A1 12/2018 Barash et al.
2019/0076167 A1 3/2019 Fantuzzi et al.
2019/0083082 A1 3/2019 Tassoni, Jr. et al.
2019/0192290 A1 6/2019 Pfenniger et al.
2019/0247627 A1 8/2019 Korkuch et al.

(56) References Cited

U.S. PATENT DOCUMENTS

| | | | |
|---|---|---|---|
| 2019/0269510 | A1 | 9/2019 | Zeng et al. |
| 2020/0078571 | A1 | 3/2020 | Kirt et al. |
| 2021/0008344 | A1 | 1/2021 | Chen et al. |
| 2021/0162171 | A1 | 6/2021 | Fitterer et al. |
| 2021/0236783 | A1 | 8/2021 | Korkuch et al. |
| 2022/0032015 | A1 | 2/2022 | Campbell et al. |
| 2022/0346950 | A1 | 11/2022 | Le et al. |
| 2023/0029387 | A1 | 1/2023 | Yadav et al. |
| 2023/0056245 | A1 | 2/2023 | Fine et al. |
| 2023/0069245 | A1 | 3/2023 | Tran et al. |
| 2023/0149674 | A1 | 5/2023 | Neumann et al. |
| 2023/0364393 | A1 | 11/2023 | Rajaram et al. |
| 2023/0381455 | A1 | 11/2023 | Fantuzzi et al. |
| 2024/0025140 | A1 | 1/2024 | Korkuch |
| 2024/0091038 | A1 | 3/2024 | Acharya |
| 2024/0299722 | A1 | 9/2024 | Ruiz et al. |
| 2025/0001139 | A1 | 1/2025 | Farrell et al. |
| 2025/0144367 | A1 | 5/2025 | Anderson et al. |
| 2025/0249213 | A1 | 8/2025 | Belcher et al. |
| 2025/0276153 | A1 | 9/2025 | Moran et al. |
| 2025/0276155 | A1 | 9/2025 | Moran et al. |
| 2025/0367411 | A1 | 12/2025 | Mak et al. |

FOREIGN PATENT DOCUMENTS

| | | | |
|---|---|---|---|
| DE | 19907646 | A1 | 8/2000 |
| EP | 0103546 | A1 | 3/1984 |
| EP | 0592410 | A1 | 4/1994 |
| EP | 0592410 | B1 | 10/1995 |
| EP | 0850607 | A1 | 7/1998 |
| EP | 1139889 | A1 | 10/2001 |
| EP | 1694398 | A2 | 8/2006 |
| EP | 1793881 | A2 | 6/2007 |
| EP | 1804860 | A2 | 7/2007 |
| EP | 2101661 | A1 | 9/2009 |
| EP | 2288403 | A2 | 3/2011 |
| EP | 2475417 | A2 | 7/2012 |
| EP | 2862590 | A1 | 4/2015 |
| EP | 2911729 | A1 | 9/2015 |
| EP | 2995268 | A1 | 3/2016 |
| EP | 3837001 | B1 | 1/2026 |
| FR | 2815844 | A1 | 5/2002 |
| JP | 2012040145 | A | 3/2012 |
| WO | 1991017720 | A1 | 11/1991 |
| WO | 1998029057 | A1 | 7/1998 |
| WO | 1999012483 | A1 | 3/1999 |
| WO | 2001049213 | A2 | 7/2001 |
| WO | 2001054625 | A1 | 8/2001 |
| WO | 2001076510 | A2 | 10/2001 |
| WO | 2002022054 | A1 | 3/2002 |
| WO | 2002036048 | A1 | 5/2002 |
| WO | 2002047575 | A2 | 6/2002 |
| WO | 2002060352 | A1 | 8/2002 |
| WO | 2003030776 | A2 | 4/2003 |
| WO | 2003047468 | A1 | 6/2003 |
| WO | 2004019825 | A1 | 3/2004 |
| WO | 2004037333 | A1 | 5/2004 |
| WO | 2005084595 | A1 | 9/2005 |
| WO | 2005102015 | A2 | 11/2005 |
| WO | 2006032051 | A2 | 3/2006 |
| WO | 2006111391 | A1 | 10/2006 |
| WO | 2006138173 | A2 | 12/2006 |
| WO | 2007047488 | A2 | 4/2007 |
| WO | 2007067942 | A1 | 6/2007 |
| WO | 2008147964 | A1 | 12/2008 |
| WO | 2009035745 | A1 | 3/2009 |
| WO | 2010121076 | A2 | 10/2010 |
| WO | 2013044942 | A1 | 4/2013 |
| WO | 2014140093 | A1 | 9/2014 |
| WO | WO-2015063497 | A1 | 5/2015 |
| WO | 2018148488 | A1 | 8/2018 |
| WO | WO-2018204486 | A1 | 11/2018 |
| WO | WO-2019199692 | A1 | 10/2019 |
| WO | 2022026026 | A1 | 2/2022 |
| WO | WO-2024205785 | A1 | 10/2024 |
| WO | WO-2024226928 | A1 | 10/2024 |
| WO | WO-2024263844 | A1 | 12/2024 |
| WO | WO-2025029777 | A1 | 2/2025 |
| WO | WO-2025048911 | A1 | 3/2025 |
| WO | WO-2025171203 | A1 | 8/2025 |

* cited by examiner

DILATOR WITH ENCAPSULATION FEATURE FOR SHEATH TIPS

RELATED APPLICATION

This application is a continuation of International Application No. PCT/US2023/013672, filed Feb. 23, 2023, and entitled DILATOR WITH ENCAPSULATION FEATURE FOR SHEATH TIPS, which claims priority to U.S. Provisional Patent Application No. 63/314,961, filed on Feb. 28, 2022, and entitled DILATOR WITH ENCAPSULATION FEATURE FOR SHEATH TIPS, the complete disclosures of which are hereby incorporated by reference in their entirety.

BACKGROUND

Field

The present disclosure generally relates to the field of medical devices.

Description of Related Art

Catheters and other therapy devices are often used to deliver medical devices, such as prosthetic heart valves, shunts, stents, or other devices, at locations inside the body that are not readily accessible by surgery or where access without invasive surgery is desirable. An access sheath can often be used to introduce a therapy device into the desired anatomy, such as the patient's vasculature. In some instances, a tip or another portion of the access sheath includes a relatively weak structure, which can allow the sheath to expand to accommodate a therapy device.

SUMMARY

In examples, the present disclosure relates to a dilator comprising an elongate shaft configured to be received within an access sheath and an encapsulation feature disposed on a distal portion of the elongate shaft. The elongate shaft is tapered towards a distal end of the elongate shaft. Further, the encapsulation feature includes a plurality of tabs that extend toward a proximal end of the elongate shaft. The plurality of tabs are configured to cover a distal end of the access sheath when the elongate shaft is disposed within the access sheath.

In some instances, the elongate shaft includes a recessed portion configured to receive the plurality of tabs in a collapsed state. The recessed portion includes a smaller outer diameter than an outer diameter of a portion of the elongate shaft that is adjacent to the distal portion.

In some instances, the plurality of tabs are configured to collapse onto the elongate shaft to implement a collapsed state.

In some instances, the encapsulation feature includes a memory metal. Further, in some instances, the encapsulation feature includes a coupling feature configured to couple the encapsulation feature to the elongate shaft. Moreover, in some instances, the encapsulation feature is integral with the elongate shaft.

In some instances, the elongate shaft includes a tapered portion between the distal end of the elongate shaft and the encapsulation feature. The tapered portion tapers toward the distal end of the elongate shaft.

In some instances, the dilator further comprises a hub coupled to the proximal end of the elongate shaft and configured to selectively engage with the access sheath to hold the access sheath in place between the hub and the encapsulation feature.

In examples, the present disclosure relates to a medical system comprising an access sheath including a lumen, a distal end, and a proximal end, and a dilator configured to be received within the lumen. The dilator includes an elongate shaft and an encapsulation feature disposed on a distal portion of the elongate shaft. The encapsulation feature includes a plurality of tabs that extend longitudinally. The dilator is configured to implement an encapsulation state where the plurality of tabs are coupled to the distal end of the access sheath and a collapsed state where the plurality of tabs are radially collapsed on the elongate shaft.

In some instances, the elongate shaft includes a recessed portion configured to receive the plurality of tabs in the collapsed state. The recessed portion includes a smaller outer diameter than a portion of the elongate shaft that is adjacent to the distal portion.

In some instances, the encapsulation feature includes a memory metal. Further, in some instances, the encapsulation feature is integral with the elongate shaft.

In some instances, the elongate shaft is tapered between the encapsulation feature and a distal end of the elongate shaft.

In some instances, the medical system further comprises a hub coupled to a proximal end of the elongate shaft and configured to hold the access sheath in place between the hub and the encapsulation feature when the dilator is disposed within the access sheath.

In examples, the present disclosure relates to a method of accessing an anatomical feature. The method comprises attaching an encapsulation feature of a dilator to a distal end of an access sheath. The encapsulation feature includes a plurality of tabs configured to cover the distal end of the access sheath. The method further comprises advancing the access sheath with the dilator attached thereto into anatomy, distally translating the dilator to detach the encapsulation feature from the access sheath, and proximally translating the dilator to remove the dilator from the access sheath.

In some instances, the method further comprises attaching a hub of the dilator to a proximal end of the access sheath to hold the access sheath between the hub and the encapsulation feature. The advancing the access sheath occurs with the hub attached to the proximal end of the access sheath.

In some instances, the dilator includes a recessed portion configured to receive the plurality of tabs.

In some instances, the distally translating the dilator causes the plurality of tabs to collapse into the recessed portion.

In some instances, the attaching the encapsulation feature of the dilator to the distal end of the access sheath includes distally translating the dilator through the access sheath, radially expanding the plurality of tabs, proximally translating the dilator, and collapsing the plurality of tabs onto the distal end of the access sheath.

In some instances, the encapsulation feature includes memory metal.

For purposes of summarizing the disclosure, certain aspects, advantages and/or features have been described herein. It is to be understood that not necessarily all such advantages may be achieved in accordance with any particular example. Thus, the disclosed examples may be carried out in a manner that achieves or optimizes one advantage or group of advantages as taught herein without necessarily achieving other advantages as may be taught or suggested herein.

BRIEF DESCRIPTION OF THE DRAWINGS

Various examples are depicted in the accompanying drawings for illustrative purposes and should in no way be interpreted as limiting the scope of the subject matter. In addition, various features of different disclosed examples can be combined to form additional examples, which are part of this disclosure. Throughout the drawings, reference numbers may be reused to indicate correspondence between reference elements. However, the use of similar reference numbers in connection with multiple drawings does not necessarily imply similarity between respective examples associated therewith. Furthermore, the features of the respective drawings are not necessarily drawn to scale, and the illustrated sizes thereof are presented for the purpose of illustration of various aspects thereof. For example, illustrated features may be relatively smaller/larger than as illustrated in some examples/configurations.

FIGS. 3-1 illustrates a perspective view of an example encapsulation feature/component implemented with a plurality of tabs in accordance with one or more embodiments.

FIG. 3-2 illustrates a side view of the encapsulation feature from FIG. 3-1.

FIG. 7-1 illustrates an example encapsulation feature with tabs configured in an open/expanded/loading state in accordance with one or more embodiments.

FIG. 7-2 illustrates an example encapsulation feature with tabs configured in a closed/collapsed state over at least a portion of an access sheath in accordance with one or more embodiments.

FIG. 7-3 illustrates an example encapsulation feature with tabs configured in a closed/collapsed state onto an elongate shaft of a dilator in accordance with one or more embodiments.

FIGS. 8-1 through 8-3 illustrate an example flow diagram of a process for advancing an access sheath into anatomy using a dilator that includes an encapsulation feature in accordance with one or more embodiments.

FIGS. 9-1 through 9-3 illustrate images of example anatomy and devices associated with the process of FIGS. 8-1 through 8-3 to illustrate aspects of the process according to one or more implementations thereof.

DETAILED DESCRIPTION

Figure 1:
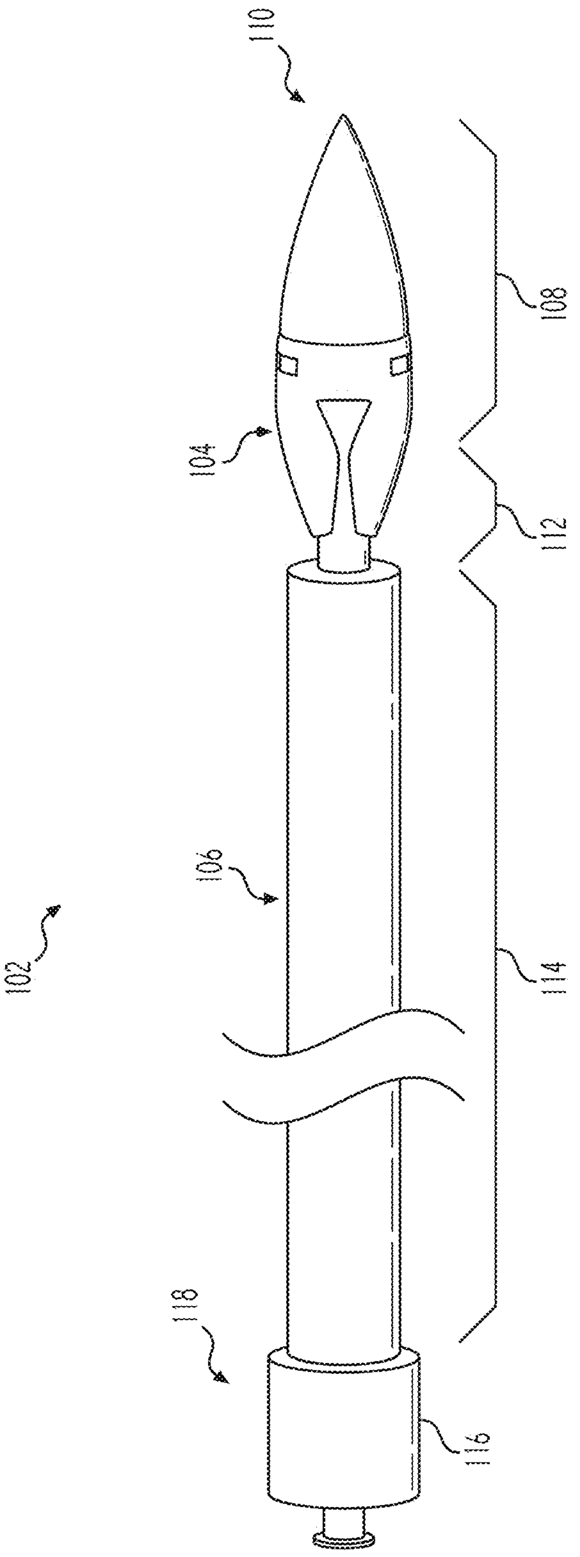
FIG. 1 illustrates an example dilator/introducer that includes an encapsulation feature according to one or more embodiments.

Any headings provided herein are for convenience and do not necessarily affect the scope or meaning of the subject matter.

Although certain examples are disclosed below, the subject matter extends beyond the specifically disclosed examples to other alternative examples and/or uses and to modifications and equivalents thereof. Thus, the scope of the claims that may arise here from is not limited by any of the particular examples described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain examples; however, the order of description should not be construed to imply that these operations are order dependent. Additionally, the structures, systems, and/or devices described herein may be embodied as integrated components or as separate components. For purposes of comparing various examples, certain aspects and advantages of these examples are described. Not necessarily all such aspects or advantages are achieved by any particular example. Thus, for example, various examples may be carried out in a manner that achieves or optimizes one advantage or group of advantages as taught herein without necessarily achieving other aspects or advantages as may also be taught or suggested herein.

Certain standard anatomical terms of location are used herein to refer to the anatomy of animals, and namely humans, with respect to the examples. Although certain spatially relative terms, such as "outer," "inner," "upper," "lower," "below," "above," "vertical," "horizontal," "top," "bottom," and similar terms, are often used herein to describe a spatial relationship of one device/element or anatomical structure to another device/element or anatomical structure, these terms are used herein for ease of description to describe the positional relationship between element (s)/structures(s), as illustrated in the drawings. Spatially relative terms can encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

The term "associated with" is used herein according to its broad and ordinary meaning. For example, where a first feature, element, component, device, or member is described as being "associated with" a second feature, element, component, device, or member, such description can indicate that the first feature, element, component, device, or member is physically coupled, attached, or connected to, integrated with, embedded at least partially within, or otherwise physically related to the second feature, element, component, device, or member, whether directly or indirectly.

An access sheath can be used to introduce a medical instrument/device into a patient's anatomy. For example, an access sheath can be positioned within the desired anatomy and a medical device can be advanced through the sheath to access a target location within the patient. In some cases, at least a portion of an access sheath can be designed to expand from an initial state having a first diameter to an expanded state having a second larger diameter. This can allow the sheath to be introduced into the patient with a smaller diameter and expanded to the larger diameter once positioned, thereby minimizing damage to the patient's anatomy and/or the access sheath.

In some instances, a medical device may not be able to withstand excessive push forces (e.g., due to a relatively fragile form of the device). The push force can refer to the amount of effort or force exerted axially on the medical device to allow the medical device to travel through an access sheath axially (which can cause expansion of the access sheath radially). Further, an excessive push force on the medical device can cause the medical device to abruptly eject from the access sheath. To minimize the push force needed to advance the medical device, a distal end (and/or other portions) of the access sheath can be formed of a relatively weak/delicate structure/material. However, this can cause damage to the distal end (or other portions) of the access when the access sheath is being advanced into the patient.

The present disclosure describes devices, systems, and methods relating to dilators/introducers that include encapsulation features configured to protect access sheaths, such as distal ends or other portions of the access sheaths. For example, a dilator can be coupled to an access sheath to introduce the access sheath into the desired anatomy in a manner that protects and/or provides additional support to a distal end and/or other portions of the access sheath. The dilator can include an elongate shaft configured to be received within the access sheath and an encapsulation feature disposed on a distal portion of the elongate shaft. The encapsulation feature can be configured to cover the distal end of the access sheath when the dilator is positioned within the access sheath and the access sheath is advanced into the desired anatomy. Once positioned within the anatomy, the encapsulation feature can be decoupled from the distal end of the access sheath, such as by advancing the dilator distally. The dilator can then be removed from the access sheath. Thus, the dilator can provide the access sheath with additional structure/support while the access sheath is advanced into the patient, thereby minimizing damage to the access sheath and/or the patient's anatomy. This can be useful in various contexts, such as where the access sheath is implemented as an expandable sheath that includes a relatively weak/fragile form and/or in other contexts.

FIG. 1 illustrates an example dilator/introducer 102 that includes an encapsulation feature 104 according to one or more embodiments. The dilator 102 (also referred to as "the encapsulation dilator 102") can include an elongate shaft/member 106 and the encapsulation/covering/protective/capsule feature 104 disposed on the elongate shaft 106 and configured to couple to an access sheath (not shown in FIG. 1). The dilator 102 can be configured to be disposed within a lumen in the access sheath such that a distal end portion of the dilator 102 extends beyond the distal end of the access sheath, which can permit the encapsulation feature 104 to couple to the access sheath, as discussed in further detail below. When coupled to an access sheath, the encapsulation feature 104 can at least partially cover/support/hold the distal end of the access sheath to protect the access sheath from damage when advanced into the desired anatomy, such as via a percutaneous access path.

The encapsulation feature 104 can include one or more flexible/movable members configured to selectively expand/open to allow an access sheath to be disposed at least partially underneath the encapsulation feature 104. In examples, the one or more flexible members can be configured to exert a radially inward force such that the one or more flexible members collapse toward the elongate shaft 106 of the dilator 102. For instance, the one or more flexible members can be configured to collapse/close around the elongate shaft 106 (in the absence of an access sheath or another device beneath the encapsulation feature 104), as shown in FIG. 1. In this example, the encapsulation feature 104 includes multiple tabs/fingers/projections that extend longitudinally toward a proximal end of the dilator 102. However, other types of features/components can be implemented, as discussed in further detail below.

The dilator 102 can include a distal tapered/dilation portion/section 108 configured to dilate/expand the anatomy in which the dilator 102 is inserted. The tapered portion 108 can taper towards a distal end 110 of the dilator 102 (e.g., the outer diameter of the dilator 102 can decrease towards the distal end 110 of the dilator 102). The tapered portion 108 can provide an atraumatic point for a coupled access sheath to be advanced into the desired anatomy. The tapered portion 108 can be positioned between the distal end 110 of the dilator 102 and at least a portion of the encapsulation feature 104 (e.g., a proximal end of the encapsulation feature 104). Although many examples illustrate the tapered portion 108 with particular shapes/sizes, any type of dilation shape/size can be implemented.

The dilator 102 can also include a recessed portion/shaft/portion/section 112 (also referred to as "the indentation 112") configured to receive the one or more flexible members of the encapsulation feature 104 when the one or more flexible members are collapsed/closed. The recessed portion 112 can include a smaller outer diameter/dimension than an outer diameter of another portion of the dilator 102 that is adjacent to the recessed portion 112, such as a main/medial body/shaft/portion/section 114. The main body 114 can have a relatively uniform outer diameter/dimension or another form. The recessed portion 112 can serve as a space/cavity to allow the proximal ends of the encapsulation feature 104 to collapse to a smaller outer diameter/dimension than the main body 114, thereby providing a smooth transition for the encapsulation feature 104 to be removed from an access sheath (e.g., translated proximally through the access sheath). The recessed portion 112 can sometimes be referred to as a "neck" that separates the distal tapered portion 108 from the rest of the dilator 102 (e.g., from the main body/shaft 114 of the dilator 102). Although the recessed portion 112 is illustrated in many examples, the recessed portion 112 can be eliminated in some implementations.

The dilator 102 can be implemented with separate components that are coupled to each other or a single component. In one illustration, the main body 114, the recessed portion 112, and/or the tapered portion 108 are implemented as separate components that are coupled/attached to each other. In another illustration, the dilator 102 is implemented with a single shaft with different sections having the characteristics/features of the main body 114, the recessed portion 112, and/or the tapered portion 108. For ease of discussion, one or more of the main body 114, the recessed portion 112, and/or the tapered portion 108 may be referred to as the elongate shaft 106. For example, a description of the encapsulation feature 104 being attached to the elongate shaft 106 can refer to the encapsulation feature 104 being attached to the main body 114, the recessed portion 112, and/or the tapered portion 108.

Figure 5:
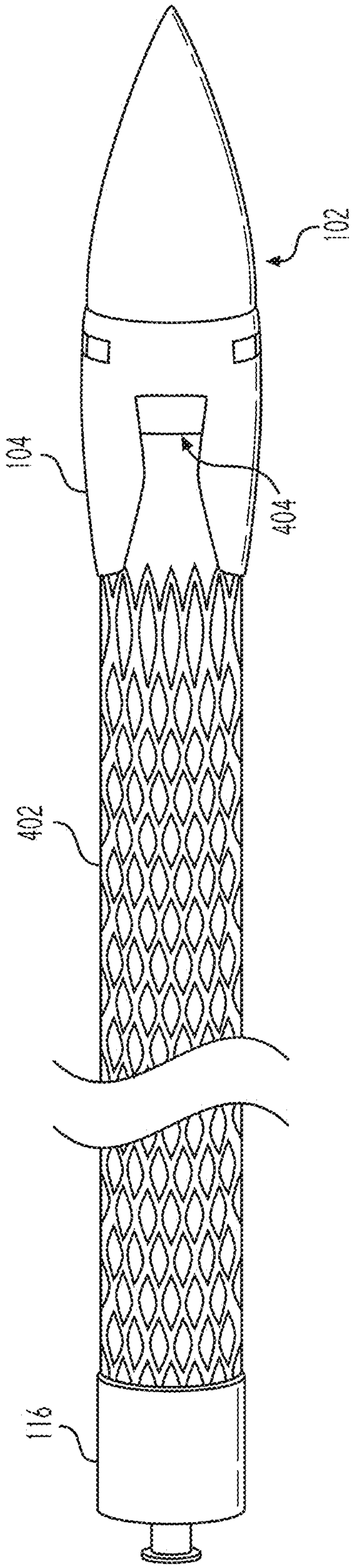
FIG. 5 illustrates an example configuration of the access sheath from FIG. 4 coupled to a dilator that includes a tab-based encapsulation feature in accordance with one or more embodiments.
Figure 6:
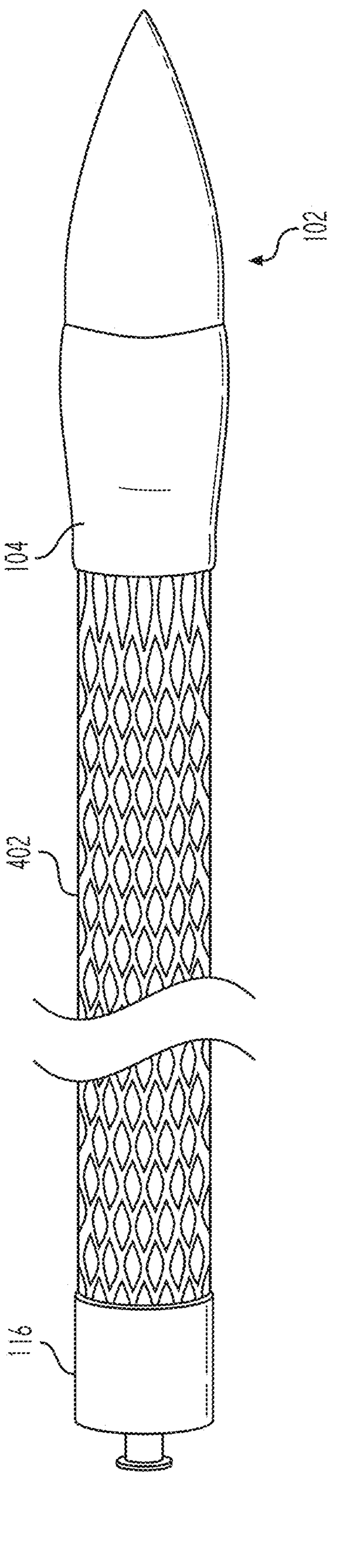
FIG. 6 illustrates an example configuration of the access sheath from FIG. 4 coupled to a dilator that includes a stretchable/non-tab-based encapsulation feature in accordance with one or more embodiments.

The elongate shaft 106 can include or be coupled to a hub 116 disposed at a proximal end 118 of the dilator 102. The hub 116 can be configured to hold an access sheath (not shown) in place while the access sheath and the dilator 102 are advanced into the patient. For example, the hub 116 can couple to a proximal end of the access sheath to maintain the access sheath in a relatively fixed position between the hub 116 and the encapsulation feature 104. This can prevent the access sheath from sliding on the dilator 102 when the access sheath is introduced into the patient. Further, the hub 116 can be configured to provide irrigation/aspiration or other functionality, such as through a lumen within the dilator 102. In some examples, the dilator 102 can include a lumen that extends from the proximal end 118 to the distal end 110, which can provide a path for another device/liquid/gas to travel. Example configurations of a dilator coupled to an access sheath are illustrated in FIGS. 5 and 6.

Although various components of the dilator 102 are discussed in the context of separate or integral components, the components of the dilator 102 can be implemented as integral or separate components. For example, one or more of the hub 116, the elongate shaft 106, and/or the encapsulation feature 104 can be implemented as a single/integral component or separate components.

Figure 2:
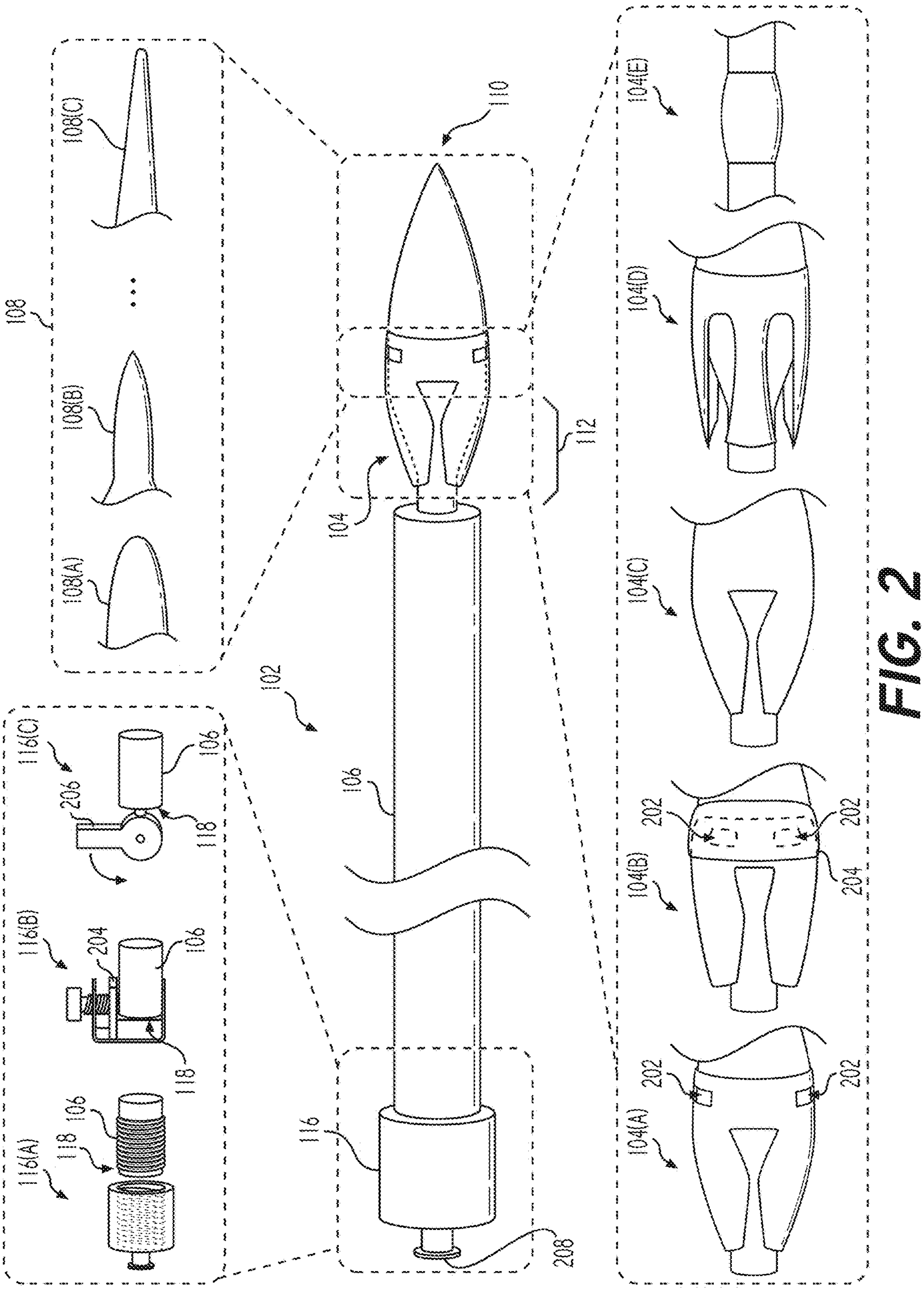
FIG. 2 illustrates example details of the dilator/introducer from FIG. 1 according to one or more embodiments.

FIG. 2 illustrates example details of the dilator 102 from FIG. 1 according to one or more embodiments. Various example features of the dilator 102 are shown in FIG. 2 (and elsewhere in the drawings) for illustrative purposes; however, the features can be implemented in other manners. Further, the dilator 102 can include other features.

As shown, the tapered portion 108 of the dilator 102 can be implemented with a variety of shapes/sizes/forms. For example, the tapered portion 108 can be implemented with any of the forms/shapes/sizes 108(A)-108(C). The tapered portion 108 can include a form/shape/size that is designed for a particular context, such as the anatomy in which the dilator 102 will be inserted, the medical procedure in which the dilator 102 will be implemented, the type of access sheath with which the dilator 102 will be used, etc. To illustrate, the tapered portion 108 can include a tapered ratio that is designed for implementation in a particular access point/medical procedure. Although various examples illustrate the encapsulation feature 104 as being coupled to the tapered portion 108, the encapsulation feature 104 can be coupled to other portions of the dilator 102, such as portions that may or may not be tapered.

The recessed portion 112 can include a form/shape/size that allows the encapsulation feature 104 to collapse around the shaft of the dilator 102. For example, the recessed portion 112 can taper back down towards the proximal end 118 of the dilator 102 such that the encapsulation feature 104 can collapse around the shaft of the recessed portion 112, as shown in FIG. 2. The recessed portion 112 can be shaped/sized/formed to meet the shape/size/form of the encapsulation feature 104, such as the inner diameter/shape of the encapsulation feature 104. In this example, the recessed portion 112 creates a step where it connects with the elongate shaft 106 (e.g., the medial portion 114 of the elongate shaft 106).

The encapsulation feature 104 can be implemented in a variety of forms/manners. In one example, illustrated at 104(A), the encapsulation feature 104 includes a plurality of tabs/fingers/projections that extend longitudinally toward the proximal end 118 of the elongate shaft 106. Here, the encapsulation feature 104(A) is implemented as a separate component from the elongate shaft 106 and is attached to the shaft 106 using an adhesive/fastener. However, the encapsulation feature 104(A) can be integral with the shaft 106. The tabs of this implementation are at least somewhat tapered toward the proximal ends of the tabs, as shown in further detail in FIGS. 3-1 and 3-2. The encapsulation feature 104(A) can include openings/holes 202 to assist in adhering/attaching the encapsulation feature 104(A) to the shaft 106, such as to permit the adhesive to outflow through the openings/holes 202. In some cases, the encapsulation feature 104(A) can be pressed onto the elongate shaft 108 and at least a portion of the elongate shaft 106 be forced out into the openings/holes 202, which can assist in holding the encapsulation feature 104(A) in place on the elongate shaft 108.

In another example, illustrated at 104(B), the encapsulation feature 104 includes a plurality of tabs/fingers/projections and an over molding/overlaid material 204 to assist in coupling the encapsulation feature 104(B) to the elongate shaft 106. The over molding 204 can cover at least a portion of the encapsulation feature 104 and/or the tapered portion 108. The over molding 204 can be disposed within the openings/holes 202 to attached to the elongate shaft 106.

In a further example, illustrated at 104(C), the encapsulation feature 104 includes a plurality of tabs/fingers/projections that are integral with the elongate shaft 106. The tabs can be formed in a variety of ways such that at least at the proximal end of the tabs can move independently relative to the elongate shaft 108. Although the implementations 104(A)-(C) include tabs that have substantially the same shape/size (e.g., tapered towards the proximal end of the tabs), the tabs can be implemented with other shapes/sizes, such as that shown at 104(D) or another form/shape/size. Further, the tabs can have different shapes/sizes/form relative to each other.

In yet another example, illustrated at 104(D), the encapsulation feature 104 includes a plurality of tabs/fingers/projections are flared towards a proximal end of the tabs. For ease of illustration, the tabs are illustrated in an expanded/open state; however, the tabs can be configured to collapse onto the elongate shaft 106 in a similar manner as the tabs discussed above for the other implementations.

In another example, illustrated at 104(E), the encapsulation feature 104 is implemented with a flexible/stretchable/moldable substance/material (sometimes referred to as "a non-tab-based encapsulation feature" or "stretchable encapsulation feature"). For instance, the encapsulation feature 104(E) can be implemented with a polymer or another flexible material that can be stretched/flexed/moved to cover the distal end of an access sheath. In examples, the encapsulation feature 104(E) can include a silicone, NEUSoft™, or another substance that has particular elasticity, tear, or other characteristics.

In examples, the encapsulation feature 104 of the implementations 104(A)-104(D) can be implemented with a metal, such as memory metal. For instance, the encapsulation feature 104 can include nitinol or another memory metal that is configured to maintain a particular form/shape (e.g., a default/initial/manufactured form). This structure/material can be useful to help the encapsulation feature 104 collapse toward the elongate shaft 106, such as to hold an access sheath during insertion of the access sheath or collapse around the elongate shaft 106 during retraction of the dilator 102 from the access sheath. In many instances, memory metal can allow the encapsulation feature 104 to automatically collapse/close inward toward the elongate shaft 106. Alternatively, or additionally, the encapsulation feature 104 can be implemented with other substances/materials, such as polymers, ceramics, etc.

Although various features are illustrated with respect to a particular implementation for the encapsulation feature 104, any of such features can be used/interchanged. Further, other features can be implemented for the encapsulation feature 104. For example, the encapsulation feature 104 can be implemented with an actuation component/system, such as a pull wire, fluid/gas, etc., that is configured to control a state of the encapsulation feature 104. To illustrate, the dilator 102 can be implemented with a pull wire that extends from the proximal end 118 through the elongate shaft 106, travels up through the distal end of the encapsulation feature 104, and travels back toward the proximal end of the encapsulation feature 104 to attach to the proximal end of the encapsulation feature 104. The pull wire can be actuated to expand or collapse tabs or other elements of the encapsulation feature 104. In another example, the dilator 102 can be implemented with a balloon that is disposed under at least a portion of the encapsulation feature 104 and is configured to expand/contract to control a state of the tabs. The balloon can be inflated/deflated via a fluid/gas passage that runs through the elongate shaft 106.

The dilator 102 can include a variety of materials/substances, such as a polymer, metal, ceramic, etc. In some examples, the encapsulation feature 104 includes a different type of substance than the rest of the dilator 102. While in other examples, the encapsulation feature 104 is implemented with the same type of substance.

As noted above, the hub/locking feature 116 can be configured to maintain/lock an access sheath (not shown) in place on the dilator 102. For example, the hub 116 can be coupled to the proximal end 118 of the elongate shaft 106 and configured to selectively engage with the access sheath to hold the access sheath in place between the hub 116 and the encapsulation feature 104. The hub 116 can implement a locked/coupled state/configuration to maintain an access sheath between the hub 116 and the encapsulation feature 104 and can implement an unlocked/decoupled state/configuration to allow the dilator 102 to be removed from the access sheath.

In one example, illustrated at 116(A), the hub 116 includes a threaded component/shaft that is configured to screw onto the proximal end 118 of the elongate shaft 106. Here, the hub 116(A) can include a larger other diameter component or another feature (relative to the diameter of the elongate shaft 106) that is configured to prevent an access sheath from sliding off the proximal end 118 of the elongate shaft 106 when the access sheath is disposed over the elongate shaft 106.

In another example, illustrated at 116(B), the hub 116 is implemented with a clamp/clip feature, such as a C-clamp or C-clip, that is configured to clamp/clip onto the proximal end 118 of the elongate shaft 106. In this example, the hub 116(B) can include a plate/coupling feature 204 configured to clamp down onto the proximal end 118 of the elongate shaft 106. The plate 204 can be coupled to a threaded shaft or another element that is configured to be screwed down/up to move the plate 204.

In yet another example, illustrated at 116(C), the hub 116 is implemented with a turn lever/knob 206 that is rotatably coupled to the elongate shaft 106 and configured to rotate relative to the elongate shaft 106. For instance, in a locked state, the lever 206 can be positioned 90 degrees relative to the longitudinal axis of the elongate shaft 106, as shown in FIG. 2. This can prevent an access sheath (not shown) from sliding off the proximal end 118 of the elongate shaft 106. In an unlocked state, the lever 206 can be positioned in line with the longitudinal axis of the elongate shaft 106 to allow an access sheath to be removed from the elongate shaft 106 (e.g., over the lever 206).

In some instances, the hub 116 can include a port 208 configured to couple/connect to a system that provides irrigation/aspiration through a lumen in the dilator 102. Additionally, or alternatively, the port 208 can provide an access path for a guidewire to slide through the lumen in the dilator 102. The lumen can extend longitudinally through the introducer 102 from the proximal end 118 to the distal end 110.

Although various examples are illustrated/discussed herein in the context of cylindrical dilators, the dilators can be implemented in other forms.

Figures 1, 3:
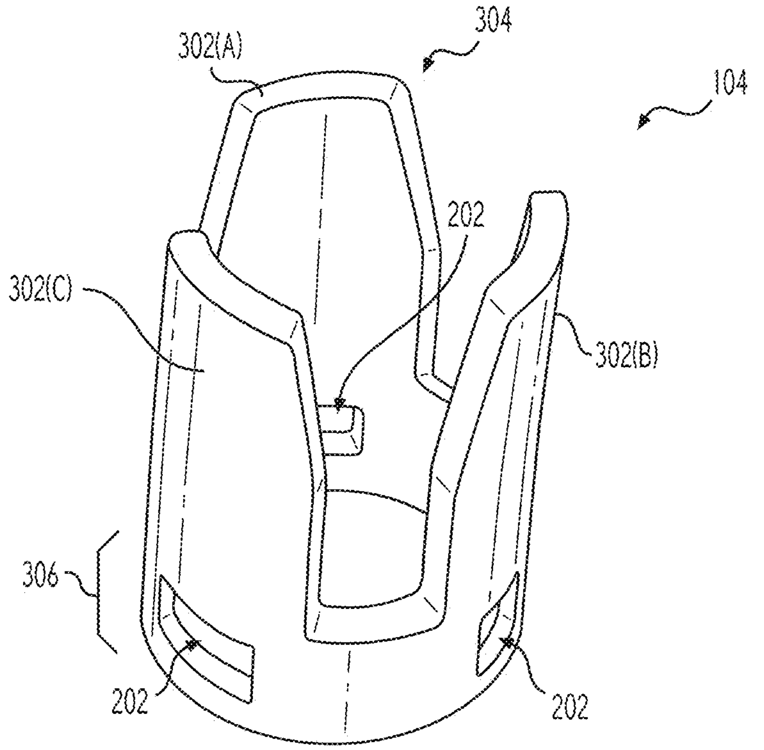
Figures 2, 3:
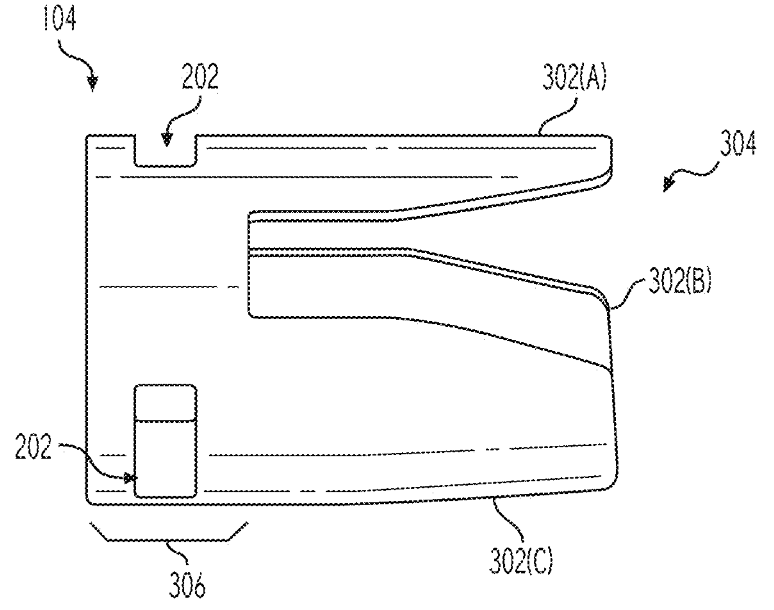

FIGS. 3-1 and 3-2 illustrate an example encapsulation feature/component 104 implemented with a plurality of tabs 302(A)-302(C) that are tapered toward a proximal end in accordance with one or more embodiments. FIG. 3-1 provides a perspective view of the encapsulation feature 104, while FIG. 3-2 provides a side view of the encapsulation feature 104. Here, the encapsulation feature 104 is implemented as a separate component from the elongate shaft 106. This example can be similar to or the same as any of the tab implementations discussed herein having tapered tabs, wherein the encapsulation feature 104 is separate from the elongate shaft 106 (e.g., implementations 104(A)-104(B) from FIG. 2).

As shown, the tabs 302 are tapered toward a proximal end 304 of the encapsulation feature 104. This can allow the tabs 302 to avoid contact with each other at the proximal end 304 when in a collapsed state. For example, the tabs 302 can collapse around a narrower shaft while avoiding contact with each other at the proximal end 304. The amount of tapering and/or length of tapering can be adjusted/configured for a particular context. Further, the tabs 302 can be spaced apart from each other circumferentially to assist in providing sufficient space for the tabs 302 to collapse inward. This can create spaces between the tabs 302. Here, the encapsulation feature 104 is implemented with three tabs; however, any number of tabs can be implemented.

One or more properties of the tabs 302 can be designed to exhibit particular characteristics. For example, a shape/length/thickness of the tabs 302, number of tabs 302, etc. can be designed to provide a particular amount of inward radial/compression force to (i) hold down a tip of an access sheath (which can exert radially outward forces, in some cases) when coupled to the access sheath, and/or (ii) allow the encapsulation feature 104 to be decoupled/removed from the tip of the access sheath without damaging the tip of the access sheath. Although the tabs 302 are illustrated with particular forms/shapes/sizes, the tabs 302 can include other forms/shapes/sizes.

The encapsulation feature 104 includes a coupling/attachment feature/section 306 configured to couple the tabs 302 to an elongate shaft, such as the elongate shaft 106 (not shown in FIGS. 3-1 and 3-2). The coupling feature 306 can be referred to as the "waist feature 306." The waist feature 306 can include the holes/openings 202 to assist in adhering/attaching the encapsulation feature 104 a component, such as to permit an adhesive to fill the openings/holes 202. As noted above, in some cases over molding can be provided within the openings 202 to assist in attaching the encapsulation feature 104 to a component. The inner diameter of the waist feature 306 can be the same as (or within a threshold amount to) an outer diameter of an elongate shaft on which the encapsulation feature 104 will be installed/attached.

The encapsulation feature 104 can be formed of a variety of materials, such as a metal (e.g., memory metal like nitinol), polymer/plastic (e.g., polyethylene terephthalate (PET), etc.), ceramic, etc. In some instances, the encapsulation feature 104 can be implemented as a shape set feature that seeks to maintain a particular shape/form. Further, in some instances, the encapsulation feature 104 can be laser cut.

Figure 4:
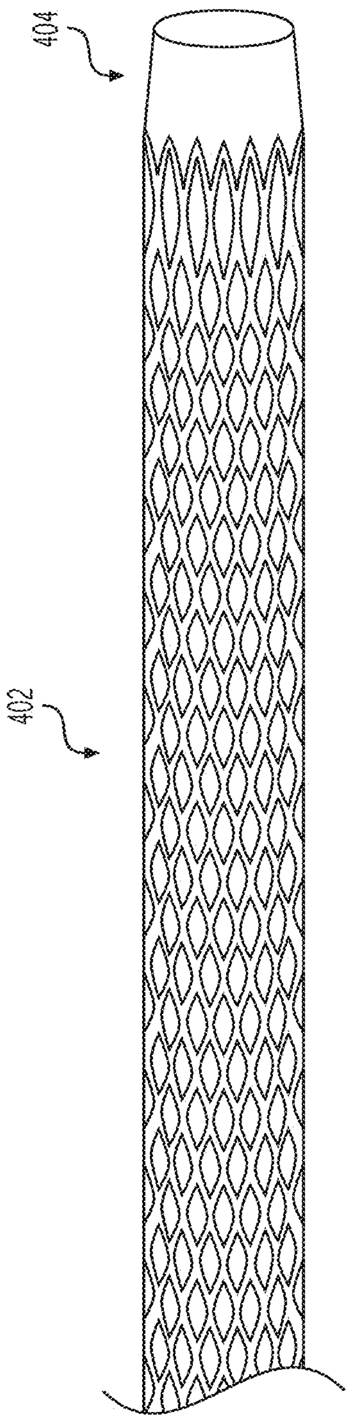
FIG. 4 illustrate an example access sheath that can be implemented with one or more introducers/dilators discussed herein in accordance with one or more embodiments.

FIG. 4 illustrate an example access sheath 402 that can be implemented with one or more introducers/dilators discussed herein and/or other components according to one or more embodiments. This example illustrates an expandable access sheath, wherein one or more portions of the access sheath are expandable from an initial diameter to a larger diameter. The access sheath 402 can be elastically/temporarily deformable/expandable or permanently deformable/expandable. In examples, an elastically/temporarily deformable/expandable sheath can refer to a sheath that seeks to maintain/return to an initial diameter/dimension when an external force is removed. Whereas a permanently deformable/expandable sheath can refer to a sheath that seeks to maintain an expanded diameter/dimension. In some cases, the access sheath 402 includes one or more permanently expandable portions and one or more temporarily/elastically expandable portions. In examples, an expandable access sheath is implemented with a mesh/braid/stent structure/shaft that is attached/coupled to a material. For instance, an expandable access sheath can include a stent frame formed of a memory metal (e.g., nitinol) with a material disposed within and/or over the stent frame. To expand an expandable access sheath from an initial inner diameter to a larger inner diameter, a sheath dilator, medical instrument, or other device can be advanced through the access sheath.

In some instances, a distal end 404 of the access sheath 402 includes a different characteristic/structure/material than one or more adjacent/other portions/sections of the access sheath 402. For example, the distal end 404 may lack some of the stent/mesh structure of an adjacent medial portion/section of the access sheath 402, as shown in FIG. 4. Here, the distal end 404 is weaker/more fragile than the adjacent portion of the access sheath 402. In examples, by having a weaker/more fragile structure at the distal end 404, an amount of push force needed to advance an instrument distally out the distal end 404 of the access sheath 402 can be reduced, which can prevent damage to the instrument and/or the access sheath 402. Further, this can minimize damage to the patient's anatomy, by avoiding the instrument from abruptly ejecting from the distal end 404 of the access sheath 402. However, the distal end 404 can be implemented with a stronger/less fragile (or same) characteristic/structure/material than other portions of the access sheath 402. In examples, the distal end 404 of the access sheath 402 is configured to flare outward (e.g., radially expand due to the structure/material of the distal end 404). Here, a dilator with an encapsulation feature (as discussed herein) can be coupled to the distal end 404 to temporarily hold down/prevent the distal end of 404 from flaring outward while the access sheath 402 is advanced into the patient.

Although various examples are illustrated/discussed herein in the context of cylindrical sheaths, the sheaths can be implemented in other forms.

FIG. 5 illustrates an example configuration of the access sheath 402 from FIG. 4 coupled to the dilator 102 (also referred to collectively as "a medical system"), wherein the dilator 102 is implemented with a tab-based encapsulation feature 104 in accordance with one or more embodiments. As shown, the access sheath 402 is disposed over the introducer 102 between the hub 116 and the encapsulation feature 104. The distal end 404 of the access sheath 402 can be slid up under the encapsulation feature 104, such as to a point where the distal end 404 is contacting the dilator 102 (e.g., underneath the encapsulation feature 104). Here, the distal portion of the dilator 102 extends beyond the access sheath 402. The hub 116 can then be tightened against and/or disposed over the proximal end of the access sheath 402. In the configuration shown in FIG. 5, the access sheath 402 and the dilator 102 can be introduced into the patient's anatomy (e.g., percutaneously through various tissue layers) in a form that provides additional support to the access sheath 402. For example, the encapsulation feature 104 of the dilator 102 can protect the distal end 404 of the access sheath 402 and/or the medial portion 114 of the dilator 102 (not shown in FIG. 5) can provide support to the access sheath 402.

In examples, the dilator 102 and the access sheath 402 can be sized such that the devices form a relatively tight fit to each other. For example, the inner diameter of the access sheath 402 and an outer diameter of the dilator 102 (e.g., the medial portion 114) can be dimensioned to be relatively close/the same in size (e.g., within a threshold amount to each other). The relatively tight fit of the dilator 102 and the access sheath 104 can assist in providing the access sheath 402 with additional structure/support when the access sheath 402 is advanced into the desired anatomy.

FIG. 6 illustrates an example configuration of the access sheath 402 from FIG. 4 coupled to the dilator 102 that includes a flexible/stretchable/moldable encapsulation feature 104 (e.g., non-tab structure) in accordance with one or more embodiments. As similarly discussed above, the access sheath 402 is disposed over the introducer 102 between the hub 116 and the encapsulation feature 104. Here, the encapsulation feature 104 at least partially covers the distal end of the access sheath 402. Since the encapsulation feature 104 is formed of a flexible/stretchable/moldable substance, the encapsulation feature 104 can conform to the shape of the distal end of the access sheath 402 to form a relatively tight fit with the distal end of the access sheath 402.

Figures 1, 7:
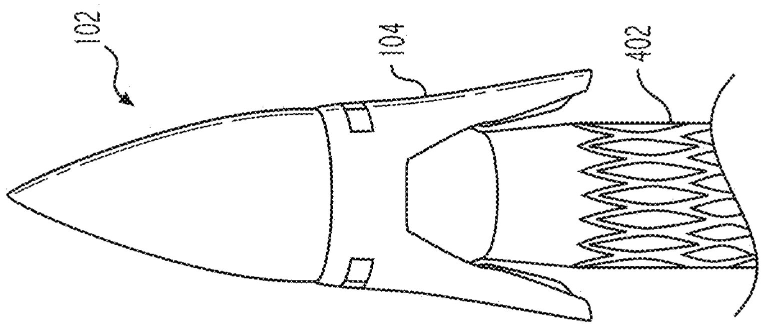
Figures 2, 7:
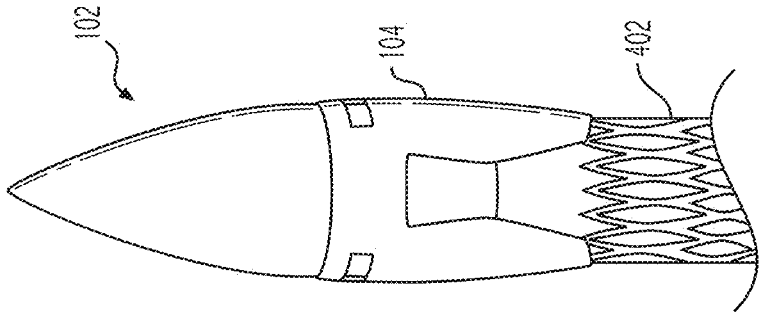
Figures 3, 7:
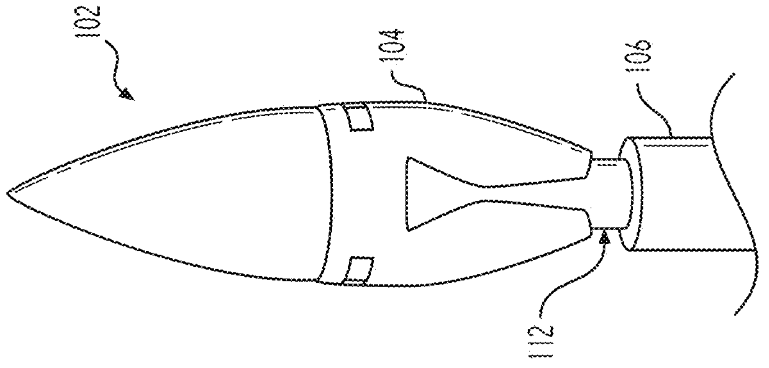

FIGS. 7-1 through 7-3 illustrate various example states/configurations of the encapsulation feature 104 of the dilator 102 in accordance with one or more embodiments. In these figures, the encapsulation feature 104 is implemented with a plurality of tabs that are configured/arranged to open/expand and close/collapse.

FIG. 7-1 illustrates the tabs 104 in a fully open/expanded/loading state, wherein the dilator 102 is configured to receive the access sheath 402. The tabs 104 can be opened/expanded to the arrangement shown using a variety of techniques, such as by a user in a manual manner, by a loading device that is configured to open/expand the tabs 104, by an actuation component (e.g., pull wire, balloon, etc.), etc. With the tabs 104 opened/expanded, the access sheath 402 can be advanced onto the dilator 102 and positioned such that at least a portion of the distal end of the access sheath 402 is underneath the tabs 104, as shown. In examples, this configuration can be referred to as a loading state, since the access sheath 402 is loaded onto the dilator 102.

FIG. 7-2 illustrates the tabs 104 in a closed/collapsed state over at least a portion of the access sheath 402. The tabs 104 can be couple to (e.g., radially collapsed onto) the access sheath 402. In some cases, the tabs 104 can automatically collapse/close onto the distal end of the access sheath 402 when a force that is used to open the tabs 104 (such as to the configuration of FIG. 7-1) is removed. In the state of FIG. 7-2, the access sheath 402 and the dilator 102 can be introduced into the desired anatomy (e.g., with the encapsulation feature 104 forming a capsule around the distal end of the access sheath 402 to protect the access sheath 402). In examples, this configuration can be referred to as a delivery/coupled/partially collapsed/encapsulation state, since the tabs 104 are coupled to/cover the access sheath 402.

FIG. 7-3 illustrates the tabs 104 in a closed/collapsed state onto the elongate shaft 106, such as within the recessed portion 112. In this configuration, the dilator 102 can be retracted from the access sheath 402. Here, the tabs 104 can be radially collapsed onto the elongate shaft 106. As shown, an outer diameter of the recessed portion 112 can have a smaller outer diameter than an outer diameter of the adjacent portion of the elongate shaft 106. This can provide a space for the tabs 104 to collapse onto the shaft 106 and provide a relatively low-profile form. In examples, the proximal ends of the tabs 104 in the collapsed state can have the same or smaller outer diameter than the outer diameter of the adjacent portion of the elongate shaft 106 (e.g., main body 114), as shown in FIG. 7-3. Further, in examples, the largest outer diameter of the encapsulation feature 104 in the collapsed state can be smaller (or larger, in some cases) than an outer diameter of the elongate shaft 106 (e.g., main body 114) and/or than the inner diameter of the access sheath 402. The configuration of FIG. 7-3 can be referred to as the fully collapsed/closed/removal state, since the tabs 104 are collapsed onto the elongate shaft 106.

Figures 1, 8:
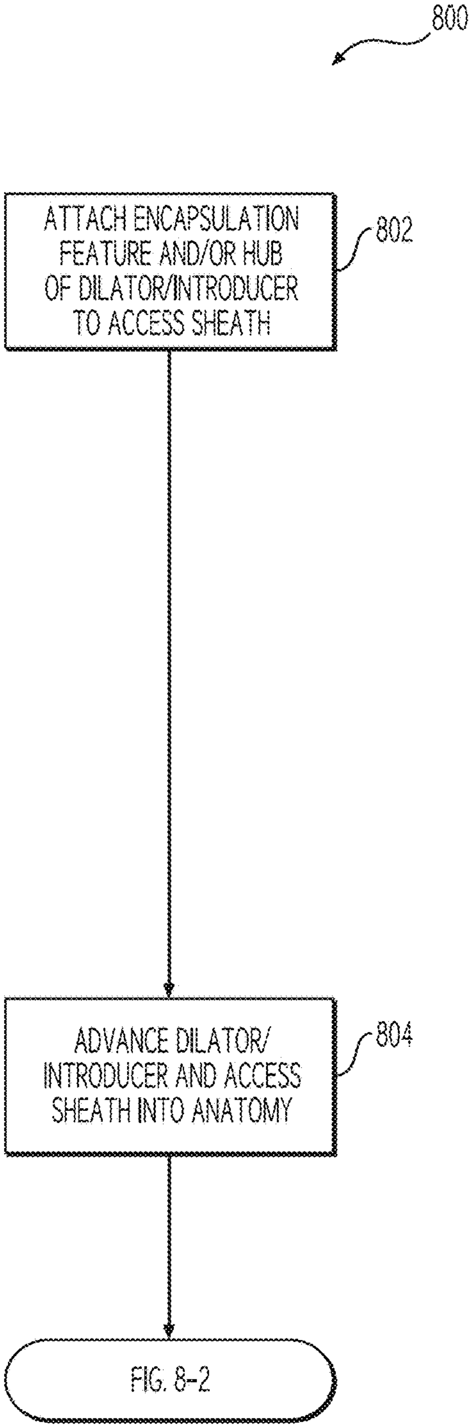
Figures 1, 9:
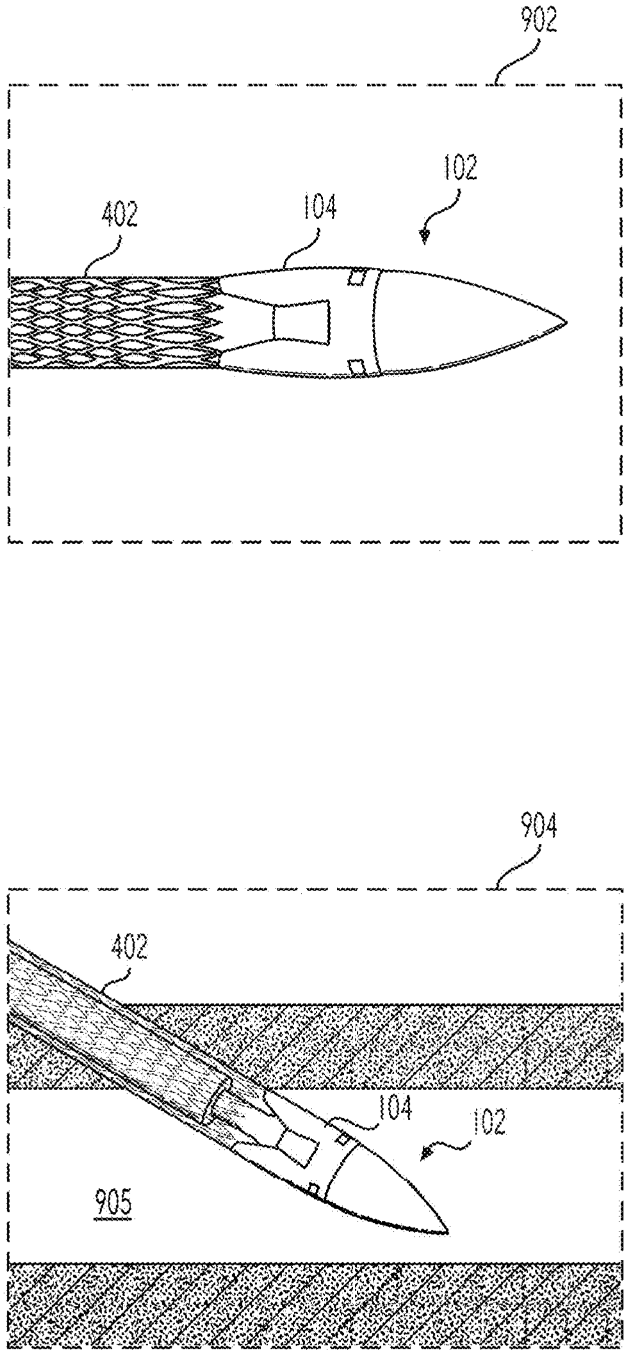
Figures 2, 8:
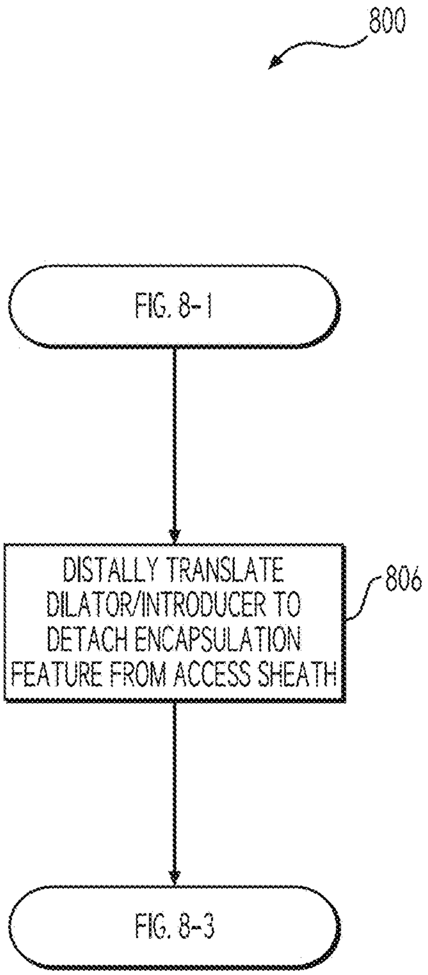
Figures 2, 9:
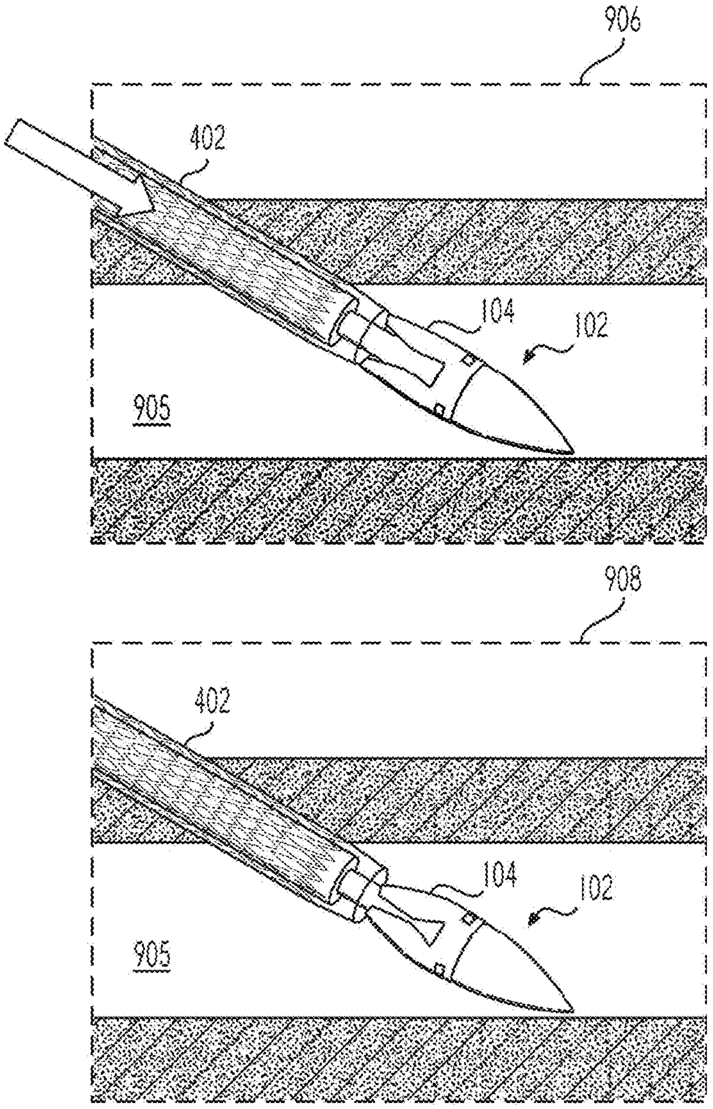
Figures 3, 8:
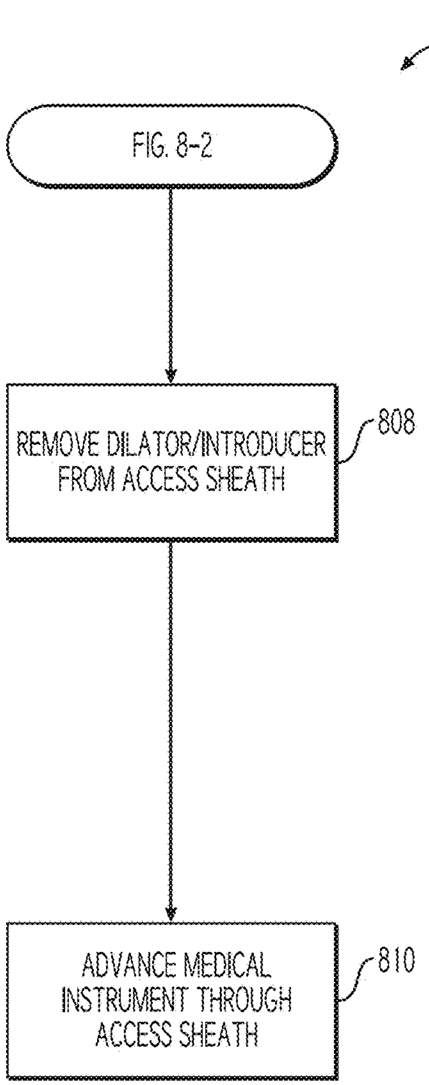
Figures 3, 9:
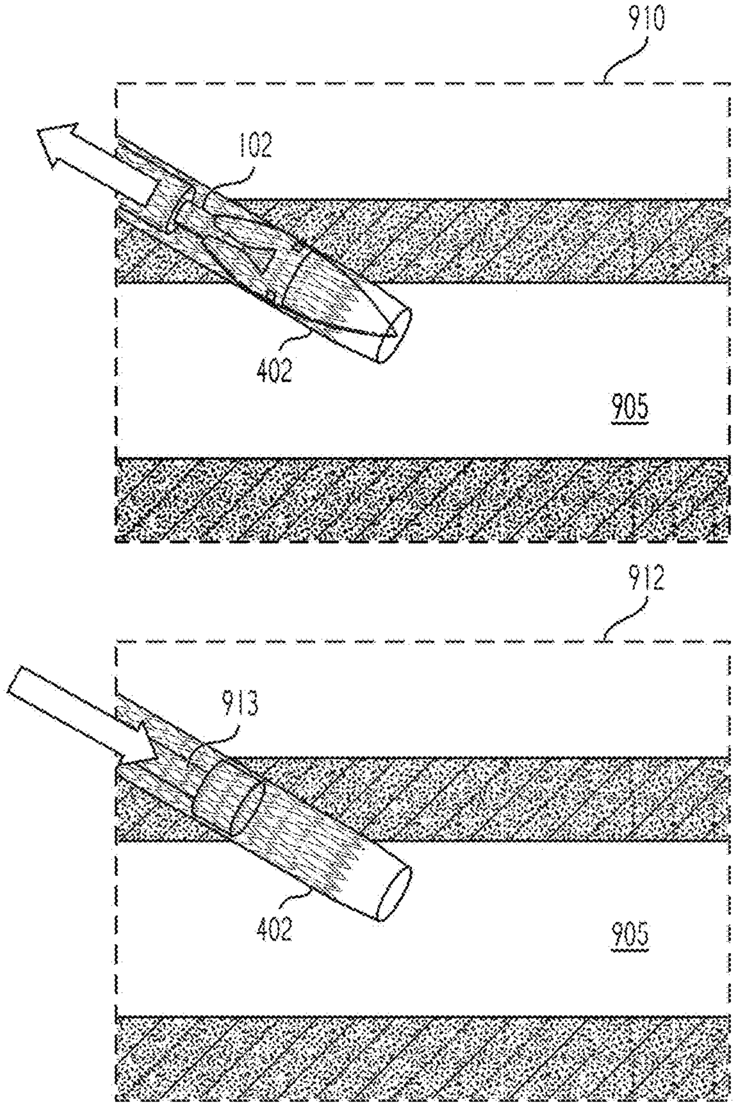

FIGS. 8-1 through 8-3 illustrate an example flow diagram of a process 800 for advancing an access sheath into an anatomical feature using a dilator that includes an encapsulation feature in accordance with one or more embodiments of the present disclosure. FIGS. 9-1 through 9-3 show images of example anatomy and devices associated with the process 800 of FIGS. 8-1 through 8-3 to illustrate aspects of the process 800 according to one or more implementations thereof. The process 800 is illustrated as a sequence of blocks. The blocks can be arranged in any order and are not necessarily limited to the particular order illustrated. The acts/operations of the blocks can be performed by a physician/user and/or a device/component/system.

In FIG. 8-1, at block 802, the process 800 includes attaching an encapsulation feature and/or a hub of a dilator/introducer to an access sheath. For example, as shown in image 902, the encapsulation feature 104 (which can be disposed on a distal portion/section of the dilator 102) can be positioned over at least a portion of a distal end of the access sheath 402. The hub 116 (not shown in FIG. 9-1) can also be coupled/attached to a proximal end of the access sheath 402 to hold/maintain the access sheath 402 between the hub 116 and the encapsulation feature 104. In some cases, the dilator 102 can be attached/joined to the access sheath 402 during preparation for a procedure. However, the dilator 102 and the access sheath 402 can be coupled/joined at other times.

In some examples where the encapsulation feature 104 is implemented with tabs (as shown in FIG. 9-1), the tabs 104 can be opened/expanded to allow the access sheath 402 to be positioned appropriately for attachment to the access sheath 402. Once opened, the access sheath 402 can be advanced distally underneath the tabs 104, and the tabs 104 can be collapsed/closed over the distal end of the access sheath 402. To illustrate, the dilator 102 can be translated distally through the access sheath 402, the tabs 104 can be radially expanded, the dilator 102 can be translated proximally by a particular amount, and the tabs 104 can be collapse onto the distal end of the access sheath 402.

Further, in some examples where the encapsulation feature 104 is implemented with a stretchable/non-tab encapsulation feature 104 (as shown in FIG. 6), the encapsulation feature 104 can be coupled to the access sheath 402 by rolling/flexing or otherwise moving the encapsulation feature 104 towards the distal end of the dilator 102. Once the encapsulation feature 104 is moved out of the way, the access sheath 402 can be advanced distally to be within proximity to the rolled encapsulation feature 104. The encapsulation feature 104 can then be rolled back/repositioned onto the distal end of the access sheath 402.

In some instances, a loading/coupling device is used to couple the encapsulation feature 104 to the access sheath 402. For example, the loading device can have a funnel-like/tapered shaft that tapers toward a distal end of the loading device. The loading device can also have a lumen with a larger inner diameter than the outer diameter of the dilator 102. The inner diameter of the loading device can also be larger than the outer diameter of the access sheath 402. To couple the encapsulation feature 104 to the access sheath 402, the loading device can be advanced over the dilator 102 such that the distal end of the loading device is positioned under the encapsulation feature 104, thereby opening/expanding the encapsulation feature 104 radially outward. The loading device can act in a wedge-like manner to be positioned underneath the encapsulation feature 104. With the encapsulation feature 104 in an open/expanded state on the loading device, the access sheath 402 can be advanced distally over the dilator 102 through the lumen in the loading device (e.g., between the loading device and the dilator 102). The access sheath 402 can be positioned beneath the encapsulation feature 104. The loading device can then be retracted proximally away from the encapsulation feature 104 to collapse/close/position the encapsulation feature 104 over the distal end of the access sheath 402.

At block 804, the process 800 includes advancing the dilator/introducer and the access sheath into the anatomy. For example, as shown in image 904, the access sheath 402 with the dilator 102 attached thereto (e.g., coupled/joined dilator and access sheath) can be inserted through the skin and/or other tissue into a blood vessel/other anatomy 905. The dilator 102 can incrementally dilate/expand the anatomy while providing an atraumatic edge/point for inserting the access sheath 402 into the blood vessel 905. The dilator 102 can assist in minimizing damage to the access sheath 402 and/or the patient's anatomy. The dilator 102 can be advanced into the patient such that at least the distal end of the access sheath 402 is located within the blood vessel 905. This can create a port/access point into the blood vessel 905 (e.g., for a therapy/delivery device to access the blood vessel 905), as discussed in further detail below. In some cases, a needle/guidewire is first inserted into the patient to create a passage/path for the dilator 102. In instances where a guidewire is implemented, the dilator 102 can be advanced over the guidewire (e.g., through a lumen in the dilator 102) to navigate the dilator 102 within the anatomy of the patient. In some case, the encapsulation feature 104 is implemented to protect or hold down the distal end of the access sheath 402, such as in cases where the distal end of the access sheath 402 has a relatively weak/fragile form and/or has a tendency to open up when no force is exerted on the distal end.

In FIG. 8-2, at block 806, the process 800 includes distally translating the dilator/introducer to detach the encapsulation feature from the access sheath. For example, as shown in image 906, the dilator 102 can be inserted farther into the access sheath 402 (e.g., the access sheath 402 can remain relatively stationary while the dilator 102 is advanced distally). The distal translation of the dilator 102 can cause the encapsulation feature 104 to detach from the access sheath 402. As the encapsulation feature 104 detaches from the access sheath 402, the encapsulation feature 104 can collapse/close onto the elongate shaft of the dilator 102, such as within a recessed portion on the elongate shaft, as shown in image 908. In examples, the hub 116 of the dilator 102 (not shown in FIG. 9-2) is unlocked/decoupled from the access sheath 402 before the dilator 102 is able to be translated distally.

In FIG. 8-3, at block 808, the process 800 includes removing the dilator/introducer from the access sheath. For example, as shown in image 910, the dilator 102 can be retracted/proximally translated to remove the dilator 102 from the access sheath 402. The access sheath 402 can be held in place or otherwise remain relatively stationary while the dilator 102 is retracted.

At block 810, the process 800 includes advancing a medical instrument through the access sheath. For example, as shown in image 912, a medical instrument 913 can be advanced through the access sheath 402 once the dilator 102 has been removed from the access sheath 402. The medical instrument 913 can include a delivery catheter and/or any other type of delivery/therapy device may be used in a medical procedure. In examples, the medical instrument 913 is navigated through the blood vessel 905 and/or other anatomy along a guidewire or otherwise to reach a target location/anatomical feature.

In some non-limiting illustrations, the process 800 is performed to deliver a prosthetic device to a target location, perform a therapy at the target location, and so on. For instance, the access sheath 402 can be inserted into an artery/vein to provide an access point for a delivery catheter or other therapy device to enter into the artery or vein. The access sheath 402 can be introduced into the artery/vein with the dilator 102 to prevent damage to the patient and/or access sheath 402. The dilator 102 can then be removed and a medical instrument can be inserted through the access sheath 402 and the artery/vein to reach a target location to deploy a medical device, perform a therapy at the target location, etc.

Any of the various systems, devices, apparatuses, etc. in this disclosure can be sterilized (e.g., with heat, radiation, ethylene oxide, hydrogen peroxide, etc.) to ensure they are safe for use with patients, and the methods herein can comprise sterilization of the associated system, device, apparatus, etc. (e.g., with heat, radiation, ethylene oxide, hydrogen peroxide, etc.).

ADDITIONAL DESCRIPTION OF EXAMPLES

Example 1: A dilator comprising: an elongate shaft configured to be received within an access sheath, the elongate shaft being tapered towards a distal end of the elongate shaft; and an encapsulation feature disposed on a distal portion of the elongate shaft, the encapsulation feature including a plurality of tabs that extend toward a proximal end of the elongate shaft, the plurality of tabs being configured to cover a distal end of the access sheath when the elongate shaft is disposed within the access sheath.

Example 2: The dilator of any example herein, in particular example 1, wherein the elongate shaft includes a recessed portion configured to receive the plurality of tabs in a collapsed state, the recessed portion including a smaller outer diameter than an outer diameter of a portion of the elongate shaft that is adjacent to the distal portion.

Example 3: The dilator of example herein, in particular examples 1 or 2, wherein the plurality of tabs are configured to collapse onto the elongate shaft to implement a collapsed state.

Example 4: The dilator of any example herein, in particular examples 1-3, wherein the encapsulation feature includes a memory metal.

Example 5: The dilator of any example herein, in particular examples 1-4, wherein the encapsulation feature includes a coupling feature configured to couple the encapsulation feature to the elongate shaft.

Example 6: The dilator of any example herein, in particular examples 1-5, wherein the encapsulation feature is integral with the elongate shaft.

Example 7: The dilator of any example herein, in particular examples 1-6, wherein the elongate shaft includes a tapered portion between the distal end of the elongate shaft and the encapsulation feature, the tapered portion tapering toward the distal end of the elongate shaft.

Example 8: The dilator of any example herein, in particular examples 1-7, and further comprising a hub coupled to the proximal end of the elongate shaft and configured to selectively engage with the access sheath to hold the access sheath in place between the hub and the encapsulation feature.

Example 9: The dilator of any example herein, in particular examples 1-8, wherein the dilator is sterilized.

Example 10: A medical system comprising: an access sheath including a lumen, a distal end, and a proximal end; and a dilator configured to be received within the lumen, the dilator including an elongate shaft and an encapsulation feature disposed on a distal portion of the elongate shaft, the encapsulation feature including a plurality of tabs that extend longitudinally, the dilator being configured to implement an encapsulation state where the plurality of tabs are coupled to the distal end of the access sheath and a collapsed state where the plurality of tabs are radially collapsed on the elongate shaft.

Example 11: The medical system of any example herein, in particular example 10, wherein the elongate shaft includes a recessed portion configured to receive the plurality of tabs in the collapsed state, the recessed portion including a smaller outer diameter than a portion of the elongate shaft that is adjacent to the distal portion.

Example 12: The medical system of any example herein, in particular examples 10 or 11, wherein the encapsulation feature includes a memory metal.

Example 13: The medical system of any example herein, in particular examples 10-12, wherein the encapsulation feature is integral with the elongate shaft.

Example 14: The medical system of any example herein, in particular examples 10-13, wherein the elongate shaft is tapered between the encapsulation feature and a distal end of the elongate shaft.

Example 15: The medical system of any example herein, in particular examples 10-14, and further comprising a hub coupled to a proximal end of the elongate shaft and configured to hold the access sheath in place between the hub and the encapsulation feature when the dilator is disposed within the access sheath.

Example 16: The medical system of any example herein, in particular examples 10-15, wherein at least one of the access sheath or the dilator is sterilized.

Example 17: A method of accessing an anatomical feature, the method comprising: attaching an encapsulation feature of a dilator to a distal end of an access sheath, the encapsulation feature including a plurality of tabs configured to cover the distal end of the access sheath; advancing the access sheath with the dilator attached thereto into anatomy; distally translating the dilator to detach the encapsulation feature from the access sheath; and proximally translating the dilator to remove the dilator from the access sheath.

Example 18: The method of any example herein, in particular example 17, and further comprising attaching a hub of the dilator to a proximal end of the access sheath to hold the access sheath between the hub and the encapsulation feature, wherein the advancing the access sheath occurs with the hub attached to the proximal end of the access sheath.

Example 19: The method of any example herein, in particular examples 17 or 18, wherein the dilator includes a recessed portion configured to receive the plurality of tabs.

Example 20: The method of any example herein, in particular example 19, wherein the distally translating the dilator causes the plurality of tabs to collapse into the recessed portion.

Example 21: The method of any example herein, in particular examples 17-20, wherein the attaching the encapsulation feature of the dilator to the distal end of the access sheath includes distally translating the dilator through the access sheath, radially expanding the plurality of tabs, proximally translating the dilator, and collapsing the plurality of tabs onto the distal end of the access sheath.

Example 22: The method of any example herein, in particular examples 17-21, wherein the encapsulation feature includes memory metal.

Example 23: The method of any example herein, in particular examples 17-22, wherein at least one of the dilator or the access sheath is sterilized.

ADDITIONAL EXAMPLES

Depending on the example, certain acts, events, or functions of any of the processes or algorithms described herein can be performed in a different sequence, may be added, merged, or left out altogether. Thus, in certain examples, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain examples include, while other examples do not include, certain features, elements and/or steps. Thus, such conditional language is not generally intended to imply that features, elements and/or steps are in any way required for one or more examples or that one or more examples necessarily include logic for deciding, with or without author input or prompting, whether these features, elements and/or steps are included or are to be performed in any particular example. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain examples require at least one of X, at least one of Y and at least one of Z to each be present.

In examples, various features are sometimes grouped together in a single example, figure, or description thereof for the purpose of streamlining the disclosure and aiding in the understanding of one or more of the various aspects. This method of disclosure, however, is not to be interpreted as reflecting an intention that any claim require more features than are expressly recited in that claim. Moreover, any components, features, or steps illustrated and/or described in a particular example herein can be applied to or used with any other example(s). Further, no component, feature, step, or group of components, features, or steps are necessary or indispensable for each example. Thus, the scope of the subject matter herein disclosed and/or claimed below should not be limited by the particular examples described above.

Certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, terms (including technical and scientific terms) used herein can have the same meaning as commonly understood by one of ordinary skill in the art to which examples belong. Furthermore, terms, such as those defined in commonly used dictionaries, can be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A dilator comprising:

an elongate shaft configured to be received within an access sheath, the elongate shaft being tapered towards a distal end of the elongate shaft; and an encapsulation feature comprising a generally cylindrical component disposed on a distal portion of the elongate shaft, the encapsulation feature including a plurality of tabs that extend longitudinally toward a proximal end of the elongate shaft while biased to taper inward toward the elongate shaft so as to collapse around the elongate shaft, the plurality of tabs being configured to cover a distal end of the access sheath when the elongate shaft is disposed at least partially within the access sheath.

2. The dilator of claim 1, wherein the elongate shaft includes a recessed portion configured to receive the plurality of tabs in a collapsed state, the recessed portion including a smaller outer diameter than an outer diameter of a portion of the elongate shaft that is adjacent to the distal portion.

3. The dilator of claim 1, wherein the plurality of tabs are configured to collapse onto the elongate shaft to implement a collapsed state.

4. The dilator of claim 1, wherein the encapsulation feature includes a memory metal.

5. The dilator of claim 1, wherein the encapsulation feature includes a coupling feature configured to couple the encapsulation feature to the elongate shaft.

6. The dilator of claim 1, wherein the encapsulation feature is integral with the elongate shaft.

7. The dilator of claim 1, wherein the elongate shaft includes a tapered portion between the distal end of the elongate shaft and the encapsulation feature, the tapered portion tapering toward the distal end of the elongate shaft.

8. The dilator of claim 1, and further comprising a hub coupled to the proximal end of the elongate shaft and configured to selectively engage with the access sheath to hold the access sheath in place between the hub and the encapsulation feature.

9. A medical system comprising:

an access sheath including a lumen, a distal end, and a proximal end; and a dilator configured to be received within the lumen, the dilator including an elongate shaft and an encapsulation feature comprising a generally cylindrical component disposed on a distal portion of the elongate shaft, the encapsulation feature including a plurality of tabs that extend longitudinally toward a proximal end of the elongate shaft while tapering inward toward the elongate shaft so as to collapse around the elongate shaft, the dilator being configured to implement an encapsulation state where the plurality of tabs are coupled to the distal end of the access sheath and a collapsed state where the plurality of tabs are radially collapsed on the elongate shaft.

10. The medical system of claim 9, wherein the elongate shaft includes a recessed portion configured to receive the plurality of tabs in the collapsed state, the recessed portion including a smaller outer diameter than a portion of the elongate shaft that is adjacent to the distal portion.

11. The medical system of claim 9, wherein the encapsulation feature includes a memory metal.

12. The medical system of claim 9, wherein the encapsulation feature is integral with the elongate shaft.

13. The medical system of claim 9, wherein the elongate shaft is tapered between the encapsulation feature and a distal end of the elongate shaft.

14. The medical system of claim 9, and further comprising a hub coupled to a proximal end of the elongate shaft and configured to hold the access sheath in place between the hub and the encapsulation feature when the dilator is disposed within the access sheath.

15. A method of accessing an anatomical feature, the method comprising:

attaching an encapsulation feature of a dilator to a distal end of an access sheath, the encapsulation feature comprising a generally cylindrical component including a plurality of tabs that extend longitudinally toward a proximal end of the elongate shaft while tapering inward toward the elongate shaft so as to collapse around the elongate shaft, the tabs configured to cover the distal end of the access sheath;

advancing the access sheath with the dilator attached thereto into anatomy;

distally translating the dilator to detach the encapsulation feature from the access sheath; and proximally translating the dilator to remove the dilator from the access sheath.

16. The method of claim 15, and further comprising attaching a hub of the dilator to a proximal end of the access sheath to hold the access sheath between the hub and the encapsulation feature, wherein the advancing the access sheath occurs with the hub attached to the proximal end of the access sheath.

17. The method of claim 15, wherein the dilator includes a recessed portion configured to receive the plurality of tabs.

18. The method of claim 17, wherein the distally translating the dilator causes the plurality of tabs to collapse into the recessed portion.

19. The method of claim 15, wherein the attaching the encapsulation feature of the dilator to the distal end of the access sheath includes distally translating the dilator through the access sheath, radially expanding the plurality of tabs, proximally translating the dilator, and collapsing the plurality of tabs onto the distal end of the access sheath.

20. The method of claim 15, wherein the encapsulation feature includes memory metal.

* * * * *